(12) United States Patent
Finnson et al.

(10) Patent No.: US 12,303,714 B2
(45) Date of Patent: May 20, 2025

(54) SYSTEM AND METHOD FOR AUTOMATED RADIOTHERAPY TREATMENT PLANNING

(71) Applicant: RaySearch Laboratories AB (Publ), Stockholm (SE)

(72) Inventors: Anton Finnson, Farsta (SE); Johan Sundström, Bromma (SE); Albin Fredriksson, Stockholm (SE); Kjell Eriksson, Balsta (SE); Cecilia Batinelli, Copenhagen V (DK)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 18/860,122

(22) PCT Filed: May 23, 2023

(86) PCT No.: PCT/EP2023/061666
§ 371 (c)(1),
(2) Date: Oct. 25, 2024

(87) PCT Pub. No.: WO2023/213877
PCT Pub. Date: Nov. 9, 2023

(65) Prior Publication Data
US 2025/0108232 A1 Apr. 3, 2025

(30) Foreign Application Priority Data
May 4, 2022 (EP) .................................. 22171551

(51) Int. Cl.
*A61N 5/10* (2006.01)
(52) U.S. Cl.
CPC ............ *A61N 5/103* (2013.01); *A61N 5/1047* (2013.01)
(58) Field of Classification Search
CPC .............................. A61N 5/103; A61N 5/1047
See application file for complete search history.

(56) References Cited

U.S. PATENT DOCUMENTS

2018/0028837 A1* 2/2018 Schaetti ................. A61N 5/103
2021/0244970 A1* 8/2021 Macdonald .......... A61N 5/1082

OTHER PUBLICATIONS

International Search Report and Written Opinion dated Aug. 1, 2023, European Patent Office, Rijswijk, Netherlands.
(Continued)

*Primary Examiner* — David P Porta
*Assistant Examiner* — Meenakshi S Sahu
(74) *Attorney, Agent, or Firm* — Noréns Patentbyrå AB

(57) ABSTRACT

Disclosed herein is a treatment planning method for generating a treatment plan for radiation therapy where a set of targets (18a-18q) are to be treated, the method using a multi-leaf collimator (MLC) (4) for shaping an arc beam (24), a gantry (2) for holding the MLC, the gantry (2) capable of rotating at least partially around a patient, a couch (6) for positioning the patient, the MLC (4) being movable and defining a collimator angle (12), the gantry (2) being movable and defining a gantry angle (10) and the couch (6) optionally being movable thereby defining a couch angle (8), the method comprising the steps of:

Providing (S05) a number of candidate arc paths (20, 20', 20", 22) having an isocenter and a maximum number of arc beams (24) for the treatment plan and, depending on the maximum number of arc beams, a maximum number of target groups (34, 34', 34", 34''', 34"");

Providing (S06) a shape and position of each target (18a-18q) of the set of targets;

Calculating (S08) a target partition (36, 36', 36") out of at least some possible target partitions of the set of targets, the at least some possible target partitions (36, 36', 36") comprising a maximum number of target groups (34, 34', 34", 34''', 34""), each of the at least some possible target partitions (36, 36', 36") comprising target groups (34, 34', 34", 34''', 34""), (Continued)

Determining (S09) a cost for each target group (34, 34', 34", 34'", 34"") of the possible target partition (36, 36', 36"), taking into account a candidate arc path (20, 20', 20", 22), at least one gantry angle (10) and at least one MLC angle (12) for each target group (34, 34', 34", 34'", 34"") of a possible target partition (36, 36', 36");

Determining (S10) a cost for the possible target partition (36, 36', 36") and current candidate arc path (20, 20', 20", 22) by summing the costs of the target groups (34, 34', 34", 34'", 34"") of the possible target partition (36, 36', 36");

Repeating (S12) the calculating (S08), determining (S09) and summing (S10) step for each of the at least some possible target partitions (36, 36', 36") and at least some of the candidate arc paths (20, 20', 20", 22), and Selecting (S13) the optimal target partition (36, 36', 36") and candidate arc paths (20, 20', 20", 22) with the lowest sum of cost for the treatment plan.

20 Claims, 9 Drawing Sheets

(56) References Cited

OTHER PUBLICATIONS

Extended European Search Report dated Sep. 12, 2022, Munich, Germany.

\* cited by examiner

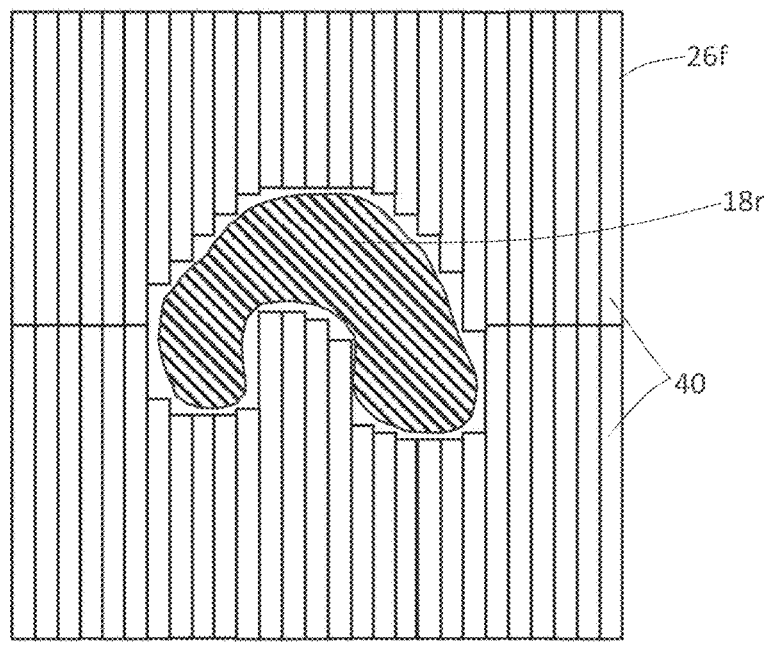
Fig. 6b
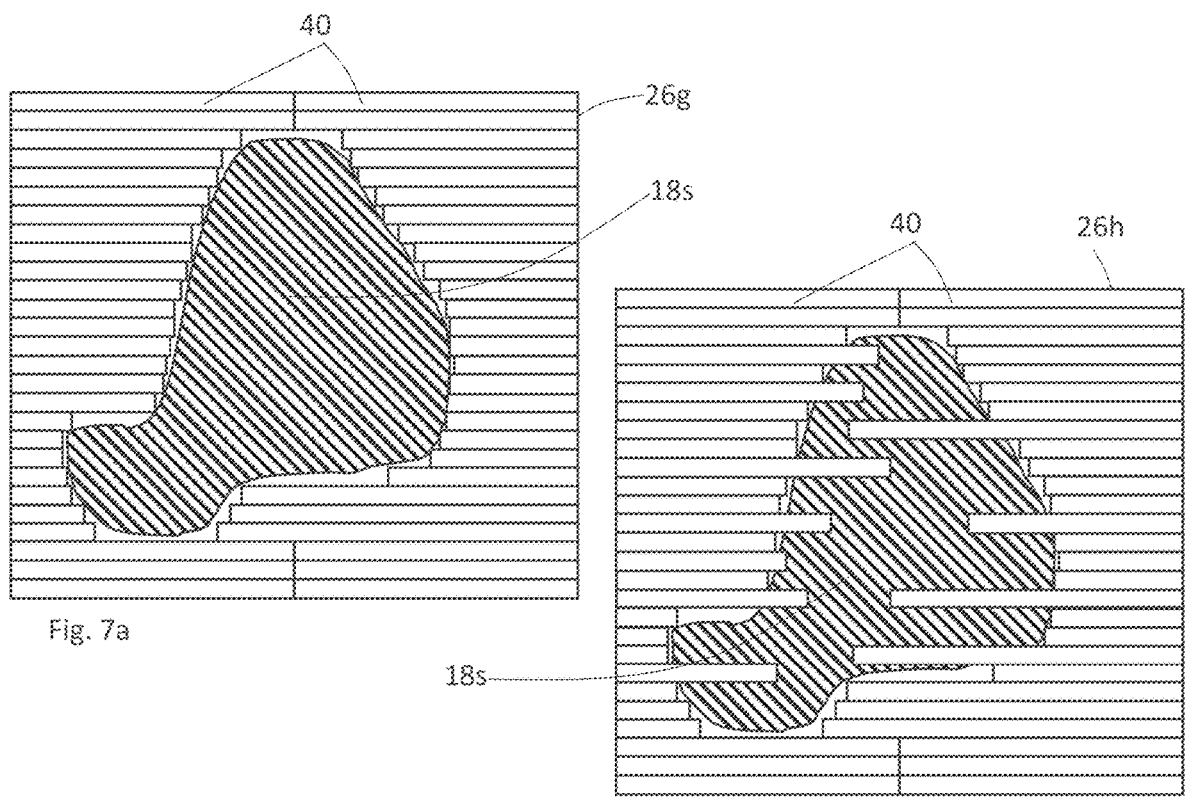
Fig. 7a
Fig. 7b

SYSTEM AND METHOD FOR AUTOMATED RADIOTHERAPY TREATMENT PLANNING

TECHNICAL FIELD

The present invention relates to a system and a method for radiation therapy treatment planning, in particular it relates to a system and a method for automated stereotactic radio surgery planning for multiple metastases (mets) and also to a treatment method thereof.

BACKGROUND

It is known in radiation therapy treatment to use beams of photons, electrons or protons or other ions and directing them towards a treatment area of a patient to treat that area or volume. The shape of the beam is normally chosen in such a way that the area to be treated receives the desired dose while limiting the dose to surrounding tissue. In particular, sensitive organs, known as organs at risk, should be protected as much as possible. To achieve this, a gantry that can rotate around the patient is often used to provide the radiation in beams from different angles, in such a way that all beams will reach the target while each part of the surrounding tissue will receive dose from only one or a few beams or, in the case of arc beams, to a lesser extent than the target. The gantry may be able to rotate fully around the patient, or rotate partially along a fraction of the circumference. The gantry may provide radiation in a continuous arc as it moves around the patient, or stop to deliver static beams at certain angles. A treatment fraction may be composed of multiple arcs or static beams, or a combination thereof. The patient couch, on which the patient is arranged and fixated, may also rotate during radiation delivery or between the delivery of static beams or arc beams, in order to modify the direction of irradiation relative to the patient. There are other means for varying the beam direction, for example, the radiation source may be mounted on a movable robotic arm, but for the purpose of this discussion the gantry is used as an illustrative example. Typically, in radiation therapy such as photon therapy, a collimator placed in the beam plane, that is, perpendicular to the beam central axis, is used to shape the beam in order for the deposited dose to match the prescribed dose a precisely as possible. Typically, collimators are multi-leaf collimators (MLC) as explained later herein.

Planning of radiosurgery gets exponentially more difficult if multiple metastases (multimets) are present and when it is aimed to treat such multiple metastases at the same time in one treatment or treatment session using a limited number of beams in order to save treatment time. In general saving treatment time in radiation treatment has several advantages such as saving time and therewith cost, reducing discomfort for the patient and reducing the time during which the patient can potentially move and dislocate the target area, which is the tumor, out of the targeted volume.

In conventional planning of multimets radiosurgery a treatment planner usually plans and also groups multiple targets (metastases) manually taking some parameters into account. This takes time and is rather difficult due to exponentially increasing potential target groups with increasing numbers of metastasis. It also leaves uncertainty if an optimal grouping is achieved, since a manual grouping of targets is challenging due to many unknown and variable parameters, such as collimator angle, couch angle and gantry angle. In addition to these parameters, the reduction and avoidance of exposed non-target areas (ENTA) need to be taken into account during planning. Various metastasis shapes or groups of metastases can lead to ENTA issues, as explained herein referring to the figures. It is therewith a high burden for a treatment planner to optimize planning. In view of these challenges, efforts have been made to automate the planning of multimets cases.

Some automated tools and solutions do exist, but they only address a limited number of parameters, for example only certain MLC angles and/or gantry angles, and they also examine a limited amount of target groups out of a complete target set and do not take all possible groups out of a given number or targets into account.

In addition, some of the known tools and solutions struggle to deliver an equal dose or dose goal over each target of a target set due to jagged MLC windows or non-exposure and therewith a risk for non-conformal dose delivery. Moreover, when multiple metastases at different depths are treated simultaneously by a beam, they are likely to receive different doses due to the depth-dose curve of the photon beam. In radiation therapy each target, metastases or tumor should, if possible, receive a plannable radiation dose in the target, in some cases this means a uniform dose and in some case a dose with no a uniform distribution over the target for example a higher dose in the center of the target, whereby the delivered dose should be as close to a dose goal as possible. This is not always possible with prior art methods and solutions.

Another issue with prior art solutions, such as for example volumetric modulated arc therapy (VMAT), is that they allow jagged openings of the multi leaf collimator. Such non-conform openings (c.f. FIGS. 7a and 7b) can lead to problems when dose levels in target volumes need to be controlled and uniformly distributed. Generally, jagged MLC openings should be avoided. Jagged MLC openings are MLC openings where certain leaves extend much further than their neighboring leaves. With jagged leaf openings and the continuously moving gantry it is very challenging to provide a robust treatment and it is problematic to provide quality assurance. Jagged MLC openings can be avoided with the proposed method herein by using a conformal system and method, in particular using conformal arc beams. It is however to be noted that jagged MLC openings can in certain cases be advantageous since they can facilitate to reach a dose goal in the target due to additional modulation leading to more freedom.

In addition, if the objective is to create a VMAT plan, the process of optimizing such a VMAT plan is greatly simplified by starting the optimization from a high-quality conformal arc plan. Starting from a high-quality conformal arc plan typically leads to a final arc plan having a higher quality than would be obtained otherwise. As such the present invention provides a way of improving VMAT planning in stereotactic radiosurgery as well.

SUMMARY

In view of the above it is an object of the present invention to provide a method that allows to automate the planning of multimets cases and that also improves efficiency of a multimets treatment using stereotactic radiosurgery (SRS).

It is further an object to provide a method that allows to provide an optimal treatment that can provide a dose goal over an entire target, even if a set of targets need to be treated in the same treatment or treatment session using a limited number of beams.

It is further an object to provide a method that allows to save time and optimize radiation treatment of multimets.

In a first aspect of the present invention the inventors of the present invention have realized that it is possible to improve the planning process for radiation treatment of multiple metastasis using automated target grouping. Thereby a set of targets that should be treated at the same time are divided into several target groups by analyzing some or all possible target partitions of the set of targets and thereby also some or all possible target group combinations taking into account possible gantry angle and collimator angle pairs and the constant aim to avoid bridge gap openings, which term bridge gap opening is explained later herein referring to FIGS. 5a and 5b, and/or to avoid the exposure of exposed non target areas (ENTA) to radiation. In short, a bridge gap opening is a configuration of the multi-leaf collimator (MLC) when the leaves can not be conformed to two or more targets without exposing non-target tissue or non-target areas in between the targets.

In a second aspect of the present invention the inventors have realized that it is possible to perform a clustering step in order to prepare a set of targets to optimal automated grouping, if the set of targets exceeds a certain amount N of targets or if targets are positioned too far apart from another. Such a clustering step may comprise the steps of choosing a maximum number M of clusters based on the number of targets, restricting the number of targets in a cluster to less or equal than N and choosing the targets in a cluster based on a maximum allowed distance between two targets of the same cluster. The second aspect requires the input of a set of targets including their shape and position relative to one another and then an optimal clustering is delivered as output taking into account the mentioned parameters such as possible gantry angle and collimator angle pairs and geometrical parameters such as maximum allowed distance between two targets of the same cluster.

In a third aspect the invention relates to a solution for dose control blocking upon the input of an arc plan having a computed dose and a dose level goal for each target. Once the dose level goals are calculated or determined for each target, the targets with an excess dose level are blocked over a portion of the arc path or arc beam or at some control points via the MLC. This means that the leaves of the MLC are closed entirely over the targets that have an excess dose level at least at some arc beams along the candidate arc path. Optionally the monitor unit (MU) levels of the beam are altered. Following the method according to the third aspect it is possible to modify the start and stop gantry angles to avoid the presence of segments or arc beams with a completely closed MLC. As an output the method according to the third aspect delivers a modified, preferably conformal arc plan that improves the fulfillment of the dose level goals for all targets, while at the same time making use of the efficient and convenient MLC openings characteristic of a conformal arc plan.

Disclosed herein is a treatment planning method for generating a treatment plan for radiation therapy where a set of targets are to be treated. The method uses a multi-leaf collimator (MLC) for shaping an arc beam, a gantry comprising the MLC, the gantry capable of rotating at least partially around a patient and a couch, a chair or other structure intended to position the patient. The MLC is rotatable around a beam axis thereby defining a collimator angle, the gantry is rotatable around a gantry axis thereby defining a gantry angle and the couch is rotatable around a z-axis thereby defining a couch angle. The method comprises the following steps:

Providing a number of candidate arc paths having an isocenter and a maximum number of arc beams for the treatment plan and, depending on the maximum number of arc beams, a maximum number of target groups;

Providing a three-dimensional shape and position of each target of the set of targets;

Calculating a target partition out of at least some possible target partitions of the set of targets based on a current candidate arc path, the at least some possible target partitions comprising a maximum number of target groups, each of the at least some possible target partitions comprising target groups, whereby in some cases each target is part of at least one target group;

Determining, for each target group of the possible target partition, a cost, taking into account the current candidate arc path, at least one gantry angle and at least one MLC angle;

Determining a cost for the possible target partition and current candidate arc path by summing the costs of each of the target groups of the possible target partition;

Repeating the calculating, determining steps for each of the at least some target partitions and candidate arc path, and Selecting the optimal target partition and arc paths with the lowest sum of cost for the treatment plan.

It is to be noted that it is not necessary that each target is always part of at least one target group, or at least one target partition-. However, in some cases target partitions, which do fulfil this requirement may be used and configured for the treatment as the examples herein discuss.

According to the above the calculating, determining and summing does not need to be performed for each possible target partition, even though this can be done. In order to save resources, such as computing resources, only relevant target partitions may be considered. Such a selection of target partitions may for example be obtained by dynamic programming or provided in another manner, whereby one knows that the target partition selection used comprises the optimal target partition. For example, if a particular target group is known to lead to a high cost, target partitions including that group can be removed from the set of target partitions to consider.

The above-described method allows to feed a set of targets into a system, such as computer or a radiation treatment planning system, and then the method automatically calculates at least some possible target partitions for evaluation and finds the optimal target partition for the treatment. A target partition thereby includes several target groups and as one can understand a set of targets can have many target partitions. The target partitions and target groups may have the condition that each target can only be part of one group, or that each target can only be part of one group per candidate arc path, to avoid that some targets are treated more than others, which would result in too high radiation dose levels. An automatic target partitioning and therewith target grouping unburdens a treatment planner from a very complicated and time-consuming planning. It also improves the result of the treatment, since the treatment method takes all possible gantry angles, MLC angles, cost sums and for example ENTA cost sums or other costs as described below and target partitions and target groups into account. Certain limitations for the calculation may be fed into the system such as maximum number of targets in a target group and maximum number of target groups in a target partition and potentially also geometrical considerations. The geometrical considerations may for example specify that all targets of a target group have to fit into a predetermined volume so that they are arranged geometrically close to one another or that no targets in the same target group can be closer than a predetermined distance from one another. Alternatively it could be specified that the projections onto the plane perpendicular to the beam central axis of all targets of a target group have to fit into a predetermined area. Geometrical considerations or conditions may relate to a maximum and/or minimum allowed distance and/or volume.

All possible target partitions may be considered for the calculating step. Alternatively, only target partitions with less than a specified number of target groups may be considered for the calculating step. Alternatively, target partitions with a target group that is known to lead to a poor solution need not be included in the target partitions considered in the calculating step. Alternatively, at most a specified number of target partitions could be considered.

All provided candidate arc paths may be used for the optimization.

Alternatively, to candidate arc paths static fields or static beams may be considered.

In an embodiment known non-optimal target partitions, for instance target partitions that comprise all targets in one target group or that comprise at least two targets positioned far away from or very close to one another, such as more than 5-6 cm away from one another or very close such as a few mm (millimetre), may be directly excluded from the above-described optimization method.

In an embodiment the calculating step may further take at least one couch angle into account.

Taking at least one couch angle into account can further improve the outcome of the optimal target partition, since the couch angle is an additional parameter that can be adjusted.

In an embodiment the maximum number of target groups is provided by a treatment planner or any given number from 1 to 6, per candidate arc beam.

The maximum number of target groups may be based on the allowed maximum number of arc beams or vice versa.

In another embodiment the calculating step can further include dividing the arc path into control points spaced at regular intervals, each interval corresponding to a gantry angle segment, wherein at each control point an optimal MLC angle and/or an optimal couch angle is calculated. Movement constraints may be taken into account during this calculating step such as a maximum rotation speed of the MLC or a maximum angle rotation of the MLC.

Predefined control points, typically spaced at regular intervals along the arc path and thus along the gantry path may be used to further optimize the target partitioning and to choose the optimal target groups. In addition, and at each control point several MLC angles and couch angles may be considered. The control points may for example be arranged in 1°, 2° or 4° degree gantry angle intervals along the arc path. The control point distancing and therewith the regular interval distance may be chosen based on the available calculating capacity of the computer at hand.

In a further embodiment an optimal MLC opening is calculated for each control point, whereby the optimal MLC opening is chosen based on lowest cost and optimal MLC angle versus previous and following MLC angle(s) at the previous and following control point.

In line with the above an additional cost is added if the MLC angle needs to be changed in between control points.

In some methods the change of MLC angle from one control point to the next may lead to a cost addition, for example in points, since adjusting an MLC angle in between control points takes time and can be challenging. However, if a bridge gap is open or another ENTA is present in the specific MLC opening at the present control point, the cost for such situation may be higher and therewith the method may choose to rotate the MLC and provide another MLC angle in order to avoid the ENTA cost or another added cost.

In light of the above and according to an embodiment herein, the calculating step may further include dividing the arc path into control points spaced at regular intervals, each interval corresponding to a gantry angle segment, wherein the MLC angle is kept in a fixed position for each control point along the candidate arc path and wherein the cost for each candidate MLC angle is calculated for each control point to find an optimal fixed MLC angle for each candidate arc path.

In another embodiment a cost may be added if the couch angle needs to be changed in between neighboring control points.

Changing the couch angle may lead to a delay or uncertainty and therewith a cost may be added if such a change is required.

In a further embodiment the maximum number of arc beams corresponds to the maximum number of target groups.

The above may help to achieve correct dose level goals for each target and target group. This condition may further improve and reduce treatment time for the patient.

In another embodiment the arc beams may be conformal arc beams.

The use of conformal arc beams provides a clear and straightforward dose level distribution in that each target receives either radiation using the efficient and useful MLC opening characteristics of a conformal arc plan or no radiation delivery at all when the leaves are completely over the target. Conformal MLC openings are aimed to be either fully open over an entire target or fully closed but they may be open by accident, for example when they need to move over a target to be able to reach a desired position of the MLC in the next control point. During such movements speed limitations may be considered. Jagged leaf positions, where some leaves extend much farther than their neighboring leaves into an opening may be avoided. According to the third aspect of the present disclosure a full dose blocking may however be allowed, thus in certain control points some leaves of the MLC may be adjusted so that one or some targets do not receive radiation at all in order to provide dose levels that match or are at least very close to a dose level goal.

In a further embodiment the method may additionally comprise the step of retrieving the lowest cost arc beam with the lowest cost MLC angle and gantry angle pairs, typically by respecting a minimum gantry angle interval, for each target group of the optimal target partition and delivering these lowest cost arc beams, whereby each arc beam is conformed to one target group of the optimal target partition so that each target group receives one arc beam for treatment.

The minimum gantry angle interval may be provided in order to avoid that too small gantry intervals would be selected.

Providing the lowest cost arc beam or arc path with the lowest cost MLC angle and gantry angle pairs for each target group of the optimal target partition may result in the possible treatment of the multimets case at hand. Such a lowest cost arc beam may be close to initially provided candidate arc paths, but the angles may slightly vary.

The described method and/or steps may be used as a starting point for VMAT optimization. Thus, in case a treatment planner has several metastases and thus a multimet case at hand she/he may use the herein described method for optimizing a starting point for other treatment methods, such as VMAT.

In another embodiment the at least some possible target partitions are considered for various arc paths and providing an arc plan comprising arc beams and arc paths based on the optimal target partitions and lowest cost arc beams, taking into account restrictions over the maximum number of arc beams, for example a maximum number of target groups in total over the maximum number or arc beams.

The method may thus consider several arc paths for the at least some possible target partitions at the same time in order to find the best treatment plan.

In another embodiment the method may further comprise the steps of:

Receiving an arc plan and a computed dose for each target in the optimal target partition, the arc plan may comprise several arc paths;

Providing a dose level goal for each target and adjusting the arc plan so that each target gets at least the dose level goal;

Alternatively to achieve or provide a correct dose level goal for each target, blocking of the targets may be used to achieve a correct relation between the targets and then scale up or optimize control point monitor unit MU in a next step;

Identifying the targets that get a dose level that exceeds the dose level goal; and Calculating a required dose control blocking where leaves of the MLC are entirely closed for at least a part of some arc beams for the targets with a dose level that exceeds the dose level goal in order to optimize the delivery of the dose and therewith the does level goals for all targets of the optimal target partition.

The above-mentioned method in the previous paragraph may be used independent of any other disclosed method herein. The above-mentioned method may be called dose control blocking method. This dose control blocking method is as mentioned above a third aspect of the invention disclosed herein and stands alone independent of the other method steps disclosed herein. At the same time the dose control blocking method may and can be used and combined with any method step or feature disclosed herein independently of other features and method steps.

Any arc plan that can be computed or provided by a radiation treatment planning method may be used as an input method for the dose control blocking method as disclosed herein in order to achieve optimal target dose levels in a group of targets over an arc beam. In addition and in particular a conformal arc plan may be used as input to the dose control blocking method according to the previous paragraphs.

The output of the dose control blocking method may be a modified conformal arc plan whereby in some positions or control points some targets are blocked from radiation via the MLC. Typically, the MLC will be open for at least one target in each control point. In some cases, the MLC can be completely closed in some control points. By modifying start and stop gantry angle and potentially also the MLC angle, control points or beams with a completely closed collimator may be avoided, since such closed segments are wasting time during treatment. Another option is to ignore completely closed collimator or MLC segments and proceed over such segments without applying any radiation in these segments.

As explained, control points and/or start gantry angle and stop gantry angle may be chosen so that not any fully closed control points or segments, in which all targets are blocked, are present.

The amended start and stop gantry angles may be adapted and/or additionally comprise segments that are ignored due to completely closed MLC openings in these segments. Alternatively, the start and stop gantry angles may not be modified but the segments with completely closed MLC configurations or openings ignored.

In another embodiment according to the disclosure herein and according to a second aspect a clustering step is performed prior to the steps disclosed in the first aspect, if the distance between two targets exceeds a certain threshold value or if a number of targets exceeds N targets. The clustering step may comprise the steps of choosing a maximum number M of clusters based on the number of targets at hand, restricting the number of targets in a cluster to less or equal than N and choosing the targets in a cluster based on a maximum allowed distance between two targets of the same cluster or geometrical consideration or condition.

As input the position and the three-dimensional shape of the target(s) may be provided.

In another embodiment an additional cost may be added, if the total number of target groups in a current target partition exceeds a certain threshold value, such as 15 to 20 target groups.

This may lead to improved target partitions and optimized planning processes.

In another embodiment the clustering step may directly take geometrical considerations as initial condition. Thus, if it is detected or determined that two targets are too far away from another and thus exceed the threshold value for the distance, whereby the threshold value may be 6 cm, the clustering step may be initiated directly without any limitation to the number N of targets at hand. Any combination of maximum number of targets N and maximum number of clusters M and geometrical considerations or geometrical conditions may be used to initiate the clustering step.

The clustering step may be used if more than three (3) targets, more than four (4) targets and/or more than five (5) targets are present, preferably more than ten (10) to fifteen (15) targets. A clustering step reduces complexity in that the number of targets that are treated with one set of arcs or method are reduced and in that they are arranged rather close to one another geometrically. Alternatively, to the maximum allowed distance between any of two targets of the same cluster, as mentioned above a volume may be given for example in $cm^3$ in which volume all targets of one cluster need to fit so that the treatment and targeting is facilitated. These geometrical conditions such as the maximum volume or maximum allowed distance are called geometric conditions or geometric considerations.

The clustering step as mentioned above is a second aspect according to the disclosure herein and may be used independently of any other method or feature disclosed herein. The clustering step or clustering method is not connected to the first aspect or the third aspect of the invention disclosed herein. The clustering step or method may be used prior to a conventional radiation treatment such IMRT or VMAT to prepare and reduce the number of targets to be treated in one and the same treatment to a manageable level.

As an example and for better illustrating the clustering method and step an example is herewith provided. A patient having brain cancer has seven (7) metastases in his head, some of them are close to the right ear while others are close to the left eye. The maximal allowed distance between targets (metastasis) is 6 cm. The requirement is thus that all targets in a cluster have to be closer or equal to 6 cm spaced apart from one another. The maximal number of targets in one cluster is set to four (4), which corresponds to N and therewith the total number of targets seven (7) exceeds the number of targets, four (4), allowed in one cluster. The maximum number M of clusters in this case is three (3). As long as the criteria with the maximal distance of 6 cm is fulfilled, a first cluster, for example one close to the right ear, will contain 4 targets and a second cluster, for example the one close to the left eye will contain the remaining 3 targets. Although theoretically a third cluster would be allowed it is not needed since the maximum number N of four targets per cluster is not exceeded and since the 6 cm maximum allowed distance condition is not breached. Once the clusters are defined the method according to the first aspect and the third aspect or any other known radiation treatment planning may be performed.

Please note that in the above example, alternatively there may be a cluster with only one (1) target while the other two clusters comprise the remaining targets. The method will evaluate which clustering is the optimal one given the provided restraints such as maximum number of targets in one cluster and the maximum number of clusters. The restraints may depend on the available arc beams, for example specified by the treatment planner or other circumstances such as treatment time limits.

Disclosed herein is also a computer program product comprising computer readable means which, when executed in a computer, will cause the computer to perform any of the aspects or method steps disclosed herein.

Further is disclosed herein a non-transitory computer readable medium encoded with computer executable instructions which, when run in a computer device will cause the device to perform the method steps or aspects of this disclosure.

In addition to the above further disclosed herein is a computer system comprising a processor, a memory, wherein the memory comprises a computer program product according to the above or a non-transitory computer readable medium according to the above.

In this disclosure certain terms and technical specifications will be used, some of them are explained referring to the figures and some of them are herewith explained and specified:

Cost Function or Cost

The term cost function or cost in relation to radiation therapy, describes a measure of the distance or difference between the obtained and the desired plan quality. A cost function may include the clinical objectives of the radiation treatment plan and represents a critical point of the optimization process during planning. Various variables can be added to the cost or cost function, such as the exposure of non-target tissue, the exposed non-target tissue area (ENTA), bridge gap openings in the MLC and/or MLC or couch angle changes between segments or arc beams. Such variables may lead to additional costs. The value a cost or a cost function delivers may be seen as a quality index of the treatment plan. Typically, a cost function for a radiation treatment plan undergoes an optimization procedure. A cost or a cost function may be based on a dose level criterion as a physical cost function or it may be based on a biological criteria as a biological cost function. An aim of a cost function in general is to provide a treatment plan with a highly conformal dose distribution without irradiating exposed non target tissue or organs at risk. In many solutions a cost function or cost is optimized by looking for a minimum of such a cost function. Costs, cost functions or an ENTA cost can be highly complex but since the core of the invention is not lying in a cost or cost function determination, the provided explanation is sufficient to understand the aspects disclosed herein.

A cost function may include the number of arc paths used to treat a set of targets. Generally, the more arc paths used for a treatment the higher the cost as an arc path adds time to a treatment. Thus, if a certain cost level of A can be achieved with seven (7) arc paths and a first treatment plan and the same cost level A can also be achieved with only six (6) arc paths and a second treatment plan, then the second treatment plan with six (6) arc paths is advantageous and shall thus receive a lower total cost than A. A cost function dependent on the number of arc paths with a single output value may be designed in the following manner:

Let T be a threshold value, so that all ENTA-costs below T are seen as equivalent. Let the cost be defined as $$c(P,N;T)=10^5*\text{round}(c_{ENTA}(P;T),3)+N$$

where P is a target partition, N the number of arc paths (at most 99) and round(x, 3) means rounding x to 3 decimal places after the integer part. In words, this function could be formulated as follows:

One example of the cost is computed as follows: first, compute a value for the ENTA part of the cost. If the resulting value is below a threshold value T, where T is larger than or equal to zero, set the value to be exactly T. Round the value to have at most three digits after the decimal place, and then multiply the result by a hundred thousand. This guarantees we have an integer with two ending zeros. Finally, add the number of (less than a hundred) arc paths in the treatment plan to obtain the total cost. Choose the target partition with lowest total cost as the optimal target partition.

Alternatively, the cost function taking into account the number of arc paths may also be designed in the following way: First, if the cost of a partition is below a threshold value T, where T is larger than or equal to zero, set that cost to be exactly T. After this step, choose the target partition(s) with the lowest cost. If multiple target partitions have the same cost, for instance the cost T, sort the target partitions by the number of arc paths in the final treatment plan, and choose the treatment plan with the lowest number of arc paths in the final treatment plan as the optimal target partition.

Multi-Leaf Collimator

A multi-leaf collimator (MLC) comprises a frame having a rectangular opening and a number of pairs of leaves placed adjacent each other along opposing sides of the opening. The two leaves in a leaf pair are placed opposite each other and can move in such a way that they can either close a part of the opening completely or expose all or a portion of that part of the opening. Each leaf pair defines a linear portion of the MLC. Various techniques exist for calculating movement patterns for the MLC during the beam delivery. For example, in sliding window delivery, the leaves move unidirectionally across the field, with the distances between opposing leaves selected in such a way that radiation will be let through in areas that should be exposed to radiation, for an amount of time determined by a fluence map, while being blocked from other areas. Multiple sliding window leaf sweeps can be delivered in sequence without switching off the irradiation, producing a movement pattern where the leaves move back and forth over the treated region.

Another example of delivery of radiation is the step-and-shoot delivery during which the leaves of the MLC are static while the radiation beam or beam is on.

For arc beams the leaves of the MLC can typically move in any direction while the beam is on.

The MLC may be rotated to different angles around the beam central axis, to limit the beam in the most suitable way given the patient geometry. A given rotation of the MLC relative to the beam central axis is called a collimator angle. It may also be feasible to rotate the MLC to different collimator angles at different gantry angles, as the patient geometry will change depending on the beam direction and/or gantry angle. The MLC may also be rotated during the delivery of a static beam, i.e., the collimator angle may be a function of the delivery time, the gantry angle, or the cumulative monitoring units (MUs) of the beam. In today's conventional practice, the collimator angle is selected manually and kept constant over the whole arc or static beam.

Target Partition

A target partition herein may mean the division of targets into groups, independently of candidate arc paths. A target partition typically comprises several target groups. In view of that a target partition can thus vary for a set of targets and various target groups. A set of targets can thus be divided into various target groups and therewith also various target partitions. In addition, target partition may also mean a division of targets per candidate arc path. A target partition typically comprises target groups whereby each target is part of at least one target group, but it may also be allowed that not each target is part of at least one target group in some cases and especially if this leads to lower total cost or ENTA. Typically, at least one target partition is examined per candidate arc path; it may however be more than one target partition and this can be specified with the method disclosed herein.

Candidate Arc Path

A candidate arc path as to the specification herein describes and means a path along which the MLC is traveling over a patient, which path is typically in the form of an arc due to the configuration and/or design of the radiation therapy system. The candidate arc path in some ways therewith also influences or decides potential gantry angles, couch angles and/or even collimator angles. When treating a group of targets, choosing relevant candidate arc paths for the treatment is of importance in order to reduce ENTA cost for the patient and in order to provide an efficient planning of the radiation treatment. MLC openings and related cost of ENTA correlate to and with a chosen candidate arc path and iterating over grouping and target partitioning of the targets at the same time as correlating to candidate arc paths greatly improves results both for the patient and the efficiency of the treatment. Choosing a target partitioning or grouping is depending on the provided candidate arc path. The quality of a specific target partition can depend on the candidate arc path. A candidate arc path may be provided via a treatment planning system or via a physical person, such as for example medical personnel. Typically, the candidate arc paths that are or considered for the method disclosed herein, are also allowed to deviate certain degrees from the provided candidate arc path or candidate arc paths. In some cases, a candidate arc path may correspond to a couch angle. A current candidate arc path herein further means the candidate arc path that is currently examined and/or computed and/or analysed.

Arc Beam

An arc beam herein is considered to be a beam of radiation that is allowed to pass the MLC at a certain position along the trajectory of the arc path. The arc beam can be a momentarily generated beam at fixed points along the trajectory or it may be a continuous arc beam that is moving along the trajectory while the collimator leaves or collimator opening adapts depending on the target(s). In some cases the arc beam is a static beam generated at certain fixed intervals along the trajectory of the MLC and arc path or candidate arc path. The arc beam is also illustrated in the figures herein.

The method(s) according to the invention according to the first aspect, the second aspect or the third aspect can be incorporated in any known treatment planning system for improving treatment planning and reducing burden on treatment planners. The methods according to the first aspect, the second aspect or the third aspect can be used and applied in radiation treatment planning independently from one another, they can however also be used in combination with another.

BRIEF DESCRIPTION OF THE DRAWINGS

The invention will be described in more detail in the following, by way of example and with reference to the appended drawings, in which:

FIGS. 6a and 6b schematically illustrate the principle of avoiding an exposure of non-target areas (ENTA);

FIGS. 7a and 7b schematically illustrate the principle of jagged leaf openings, which the present invention seeks to avoid;

DETAILED DESCRIPTION

Figure 1:
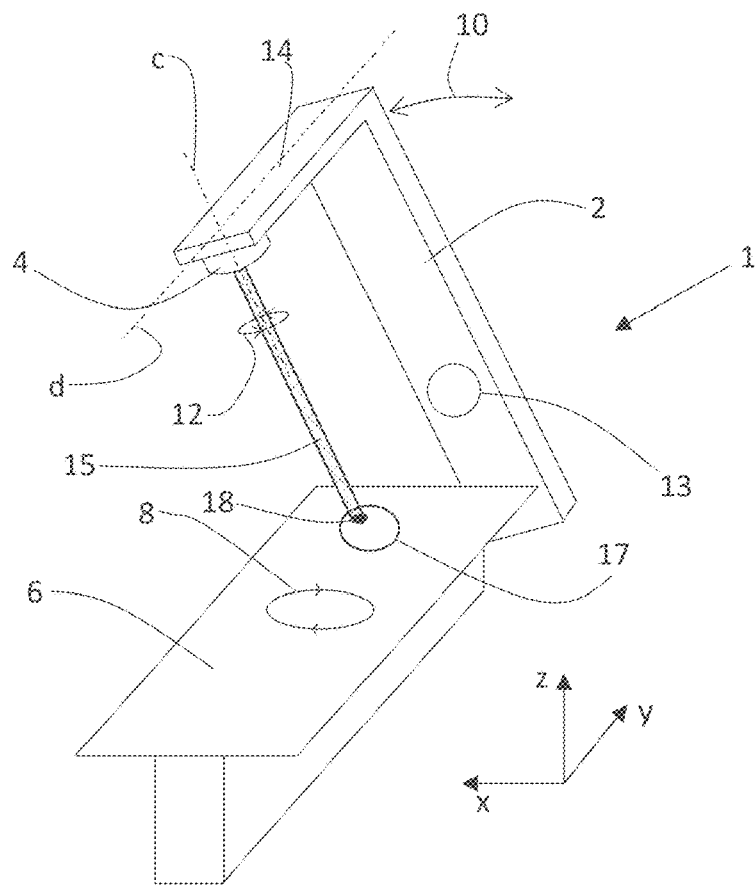
FIG. 1 schematically illustrates a setup for radiation treatment.

Turning now to the figures, which show different aspects and concepts of the invention, FIG. 1 schematically illustrates a radiation therapy treatment system 1 comprising a gantry 2 having a multi leaf collimator (MLC) 4. The radiation therapy treatment system 1 may a be used for stereotactic radio surgery (SRS). The radiation therapy treatment planning system 1 may further comprises a patient couch or couch 6, which is used to place a patient when performing radiation treatment on such a patient. For illustrative purposes the radiation therapy treatment system 1 is shown without a patient. The couch 6 can be rotated around an axis, in order to place the patient optimally during or for the treatment. In the example illustrated in FIG. 1, the couch angle 8 can be adjusted by rotating the couch 6 around the z-axis. Other movements of the couch 6 may be possible. The MLC 4 can be rotated around a collimator axis c to adjust a collimator angle 12. The collimator axis c depends on the position and therewith a gantry angle 10, since the gantry 2 can rotate around a centre of rotation 13. When a radiation beam or arc beam 15 is allowed to extend from the MLC 4 towards a body part 17 comprising a target or target volume 18, then the radiation beam 15 travels along the collimator axis c, while its shape in a cross-sectional plane is perpendicular to the collimator axis c, depends on the MLC opening as explained later herein (c.f. FIGS. 5a to 7b). The gantry may be capable of rotating all 360° around the centre of rotation 13 for irradiating of a target (not shown in FIG. 1) from different gantry angles 10. The gantry 2 may rotate around a y-axis as shown in FIG. 1. For better reaching targets the MLC 4 may be mounted on an extension arm 14 or the like, which extension arm 14 is connected to and part of the gantry 2.

It is to be noted that the angles can be defined in different ways. For the purpose of the illustrations herein the couch angle 8 is measured from the position shown in FIG. 1 counter clockwise, which means in the illustration shown in FIG. 1, the couch angle 8 is 0°. The gantry angle 10 may be measured from a horizontal plane defined by the x- and y axis, also counter clockwise, which means that the gantry angle 10 in FIG. 1 is about 110°. The collimator angle 12 may be measured starting from a line that is defined by the longitudinal axis d of the extension arm 14.

During a path along various gantry angles 10, the MLC takes in different positions along an arc path. Such arc paths are shown and described in FIG. 2.

Figure 2:
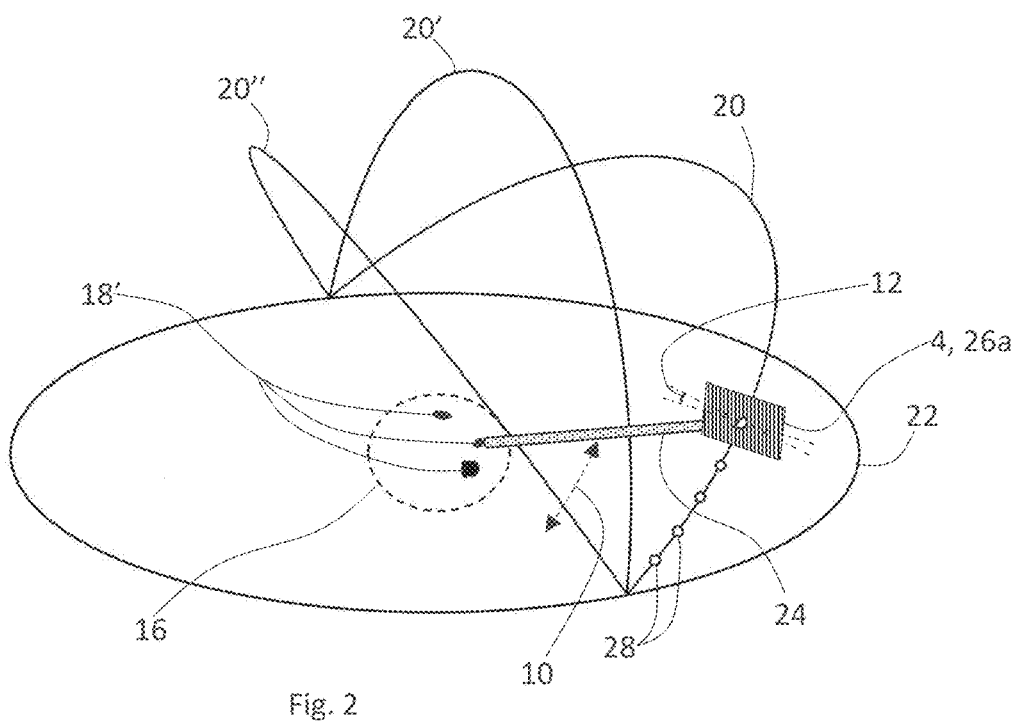
FIG. 2 schematically illustrates targets and arc paths along which the MLC is moving on a gantry for radiation treatment of the targets.

FIG. 2 illustrates a configuration where a head 16 of a patient having three metastasis 18' or targets 18' is to be treated via radiation therapy treatment. For illustrative purposes only the head 16 of the patient is shown. Several arc paths 20, 20', 20" are shown in FIG. 2. Further, another arc path 22 is shown in FIG. 2. The arc path 22 corresponds to gantry angles from 0° to 360° and a couch angle of 0°. The arc path 20 corresponds to gantry angles from 0° to 180° and a couch angle of about 45°. The arc path 20' corresponds to gantry angles from 0° to 180° and a couch angle of about 90°. Finally, the arc path 20" corresponds to gantry angles from 0° to 180° and a couch angle of about 120° or 240 (360°-120°), depending on the definition of the couch angle.

For further explanation of the radiation procedure arc path 20 is herewith used, which, as explained above, corresponds to gantry angles from 0° to 180° and a couch angle of about 45°. The arc path 20 is used to treat one of the targets 18' via an arc beam 24. For illustrative purposes only one arc beam 24 along the arc path 20 is shown. In addition, and also for illustrative purposes only one of the targets 18' is irradiated via the MLC opening 26a. The MLC 4 and therewith the MLC opening 26a is positioned at a collimator angle 12 of about 15° to 20°. The gantry angle 10 in the example shown in FIG. 2 of the arc beam 24 is about 30°. Arc beams may be delivered to the target(s) 18' from various positions at intervals along the arc path 20. These intervals may be regular intervals along the arc path. In conformal radiation therapy an arc beam 24 is delivered at least from some of the positions 28. In between two adjacent positions 28 the arc beam is typically on and the leaves 40 of the MLC 4 are not closed. In some radiation therapy methods the arc beam is however switched off over at least a part of the arc path 20, in particular during movement of the MLC 4, but the MLC opening is not closed. The invention described herein works for various solutions, including continuous arc beam delivery along the arc path 20, especially using conformal arc therapy but also for VMAT, and more generally for intensity modulated radiation therapy (IMRT), including IMRT using static fields or static beams.

In between two adjacent positions 28 or control points 28, the leaves 40 typically move linearly between their specified positions/MLC openings. In some cases the movement of the leaves 40 may be non-linear due to acceleration in the MLC 4, for example during rotation.

The positions 28 illustrated in FIG. 2 may also be called segments and alternatively they may be used as control points 28 when simulating and planning a treatment. Each control point 28 may be used to determine an optimal collimator angle 12, an optimal MLC opening 26a and even optimize the couch angle 8 with plus minus of a few degrees to optimize radiation delivery. In addition, even the arc path 20 may be optimized by a few degrees during calculation in order to find the best arc beams, arc path and therewith arc plan for the radiation delivery. Control points 28 may be spaced at regular intervals along the entire arc path 20. In the example in FIG. 2, control points 28 are spaced at 5°-7° degrees of the gantry angle 10. Any other interval spacings from 1° up to 25°, preferably 2° up to 8° may be possible and feasible. For illustrative purposes only four control points 28 are shown in FIG. 2, the reader will however understand the concept of distributing the control points 28 along the arc path 20 when calculating and determining a treatment plan. The control points 28 may also be used to determine whether or not any of the following concepts and aspects may be optimized.

Figure 3A:
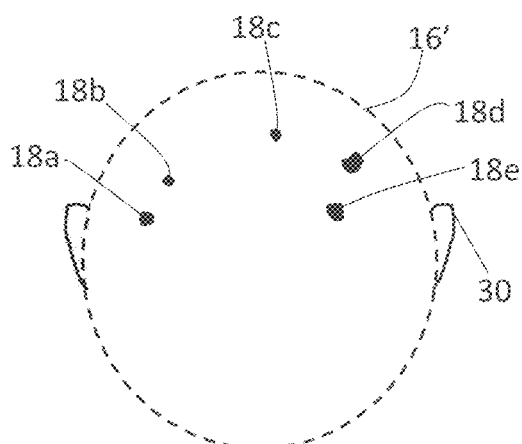
FIGS. 3a-3d schematically illustrate the principle of target partitioning or grouping via a head of a patient with seven targets.
Figure 3B:
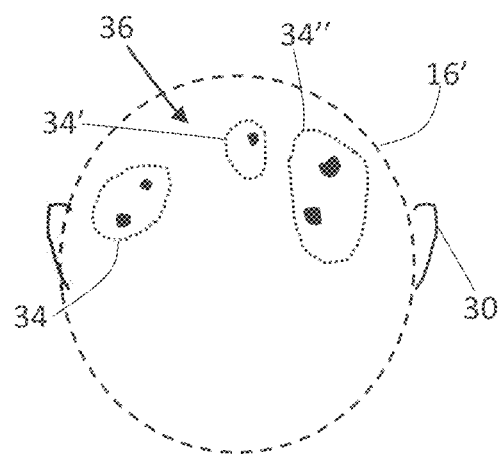
Figure 3C:
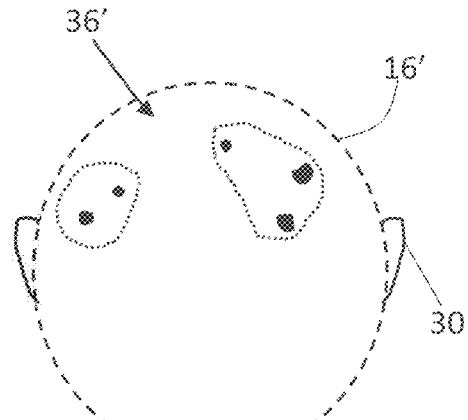
Figure 3D:
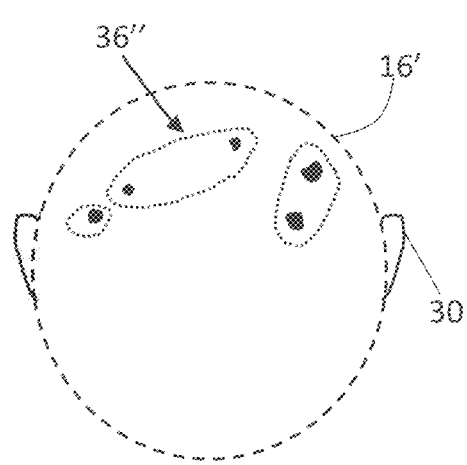

FIGS. 3a to 3d illustrate an aspect of the disclosure related to target partitioning or a target partition. FIGS. 3a to 3d illustrate a head 16' of patient with ears 30, used for illustrative purposes. The patient has totally five (5) metastasis or targets 18a-18e in the head 16'. For illustrative purposes the metastasis or targets 18a-18e are only indicated as reference numbers in FIG. 3a. FIGS. 3b to 3d disclose however the same head 16' with the same metastasis or targets 18a-18e but these FIGS. 3b to 3d explain the concept of target partitions 36, 36', 36" and target groups 34, 34', 34".

Turning now to FIG. 3b, as one may understand when grouping the five targets 18a-18e in target groups 34, 34', 34" some conditions may apply. In the example the conditions are that each target partition 36 may comprise a maximum number of three (3) target groups 34, 34', 34", whereby less than three (3) target groups 34, 34', 34" are allowed (c.f. FIG. 3c). Another condition that is however not illustrated in the FIGS. 3b, 3c and 3d is physical distancing. It may be specified that the targets 18a-18e arranged furthest away from one another in one target group 34, 34', 34" may only be spaced apart a certain distance. This distance may be specified as a condition prior to the step of target grouping and target partitioning. The distance may be from 0.5 cm up to 8 cm, 9 cm or 10 cm. In FIG. 3b a first target group 34 comprises targets 18a and 18b, a second target group 34' comprises target 18c and a third target group 34" comprises targets 18d and 18e. It is thus allowed to position only one target 18c in a target group 34'. From FIG. 3b one may understand that the target partitions 36 can be chosen in another way such as illustrated in FIGS. 3c and 3d. The target partition or a target partition is thus a division of the targets in target groups whereby each target partition stands for another target group partition or division. The target partition 36' illustrated in FIG. 3c comprises two (2) target groups, while the target partition 36" illustrated in FIG. 3d comprises three (3) target groups. The skilled person under-stands that there are many more possible target partitions than 36, 36', 36" where many can be ruled out directly due to unpracticality or the impossibility to treat such target partitions (not shown). The method disclosed herein, considers all or at least some possible target partitions using the given conditions such as maximum number of allowed target groups 34, 34', 34" in a target partition 36, 36', 36" and the maximum distance between two targets placed farthest away from one another but still in one group. This maximum distance may alternatively be specified or given as a maximum volume. The target partitioning takes further other parameters such as the concept of not exposing so called non-target areas (ENTA) to radiation as explained referring to FIGS. 5a to 6b, into account, when optimizing the treatment of multimets. FIGS. 3a to 3d refer to the first aspect of the present invention.

Figure 4A:
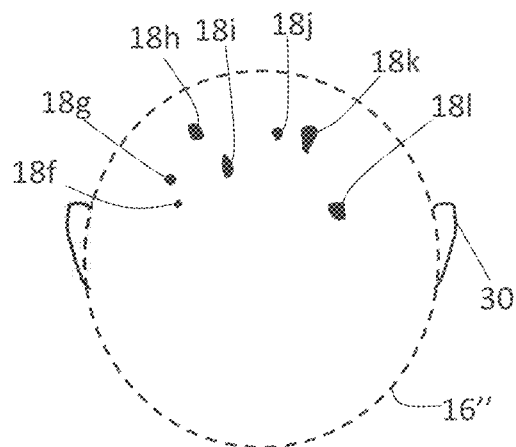
FIGS. 4a and 4b schematically illustrate the principle of target clustering.
Figure 4B:
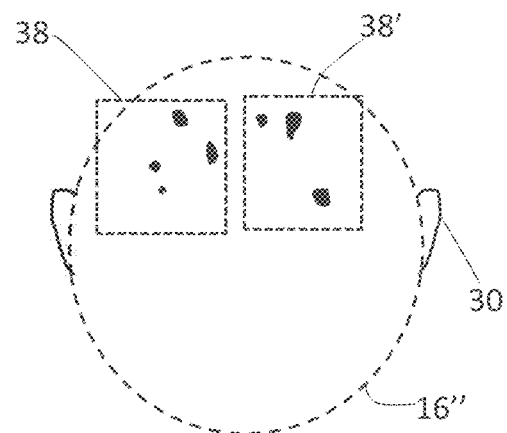

Turning now to FIGS. 4a and 4b another aspect of the present invention is herewith disclosed and explained referring to target clustering. The concept or second aspect of the disclosure is now explained using a different head 16" of a patient having seven (7) metastasis 18f-18l or targets 18f-18l.

It is to be noted that seven (7) targets 18f-18l is a rather high number but cases with up to fifteen (15) metastasis have been treated. This means that multimet cases with several targets up to fifteen (15) or even more targets can occur and the concept of clustering is herewith explained based on seven targets 18f-18l. Seven targets 18f-18l are difficult to treat with one and the same arc and thus the same isocenter. In the exemplary case shown in FIGS. 4a and 4b the targets 18f-18l are too far apart to safely be treated with the same arc/isocenter, due to rotational uncertainties, which means that the targets 18f-18l need to be divided into clusters 38, 38' so that each cluster 38, 38' can be handled separately for example by using separate or independent isocenters/arcs. The clustering step, thus dividing the targets 18f to 18l into clusters 38, 38', may be used with the radiation treatment methods disclosed herein, such as conformal treatment or IMRT, or it may be used with other radiation therapy treatment methods such as VMAT. The clusters 38, 38' may be chosen based on maximum volume allowed for targets or they may be chosen based on geometrical limitations. Another further parameter that may be considered for choosing clusters 38, 38' of targets may be a maximum number of targets, for which a target partitioning and target grouping may be allowed. Such a limitation may be chosen at four (4), five (5) or six (6) targets. The clustering step or method as disclosed in FIGS. 4a and 4b may be used in connection with the present invention or it may be used as independent method in other radiation therapy planning methods or treatments to improve outcomes of radiation therapy planning.

Figure 5A:
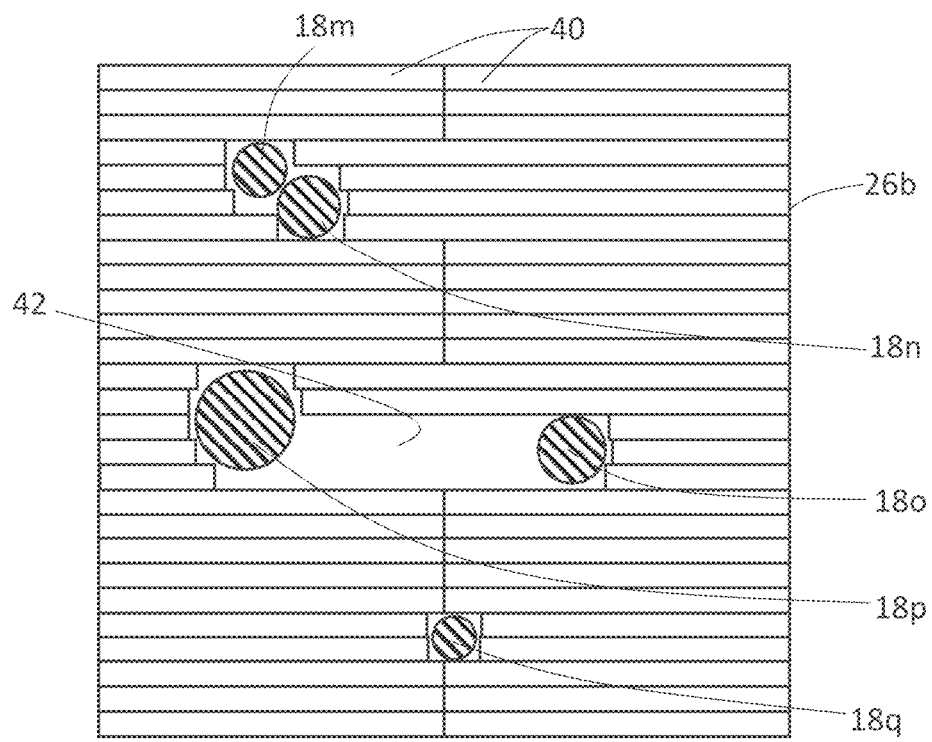
FIGS. 5a to 5c schematically illustrate the principle of using target groups to avoid bridge gap openings in a multi-leaf collimator (MLC)
Figure 5B:
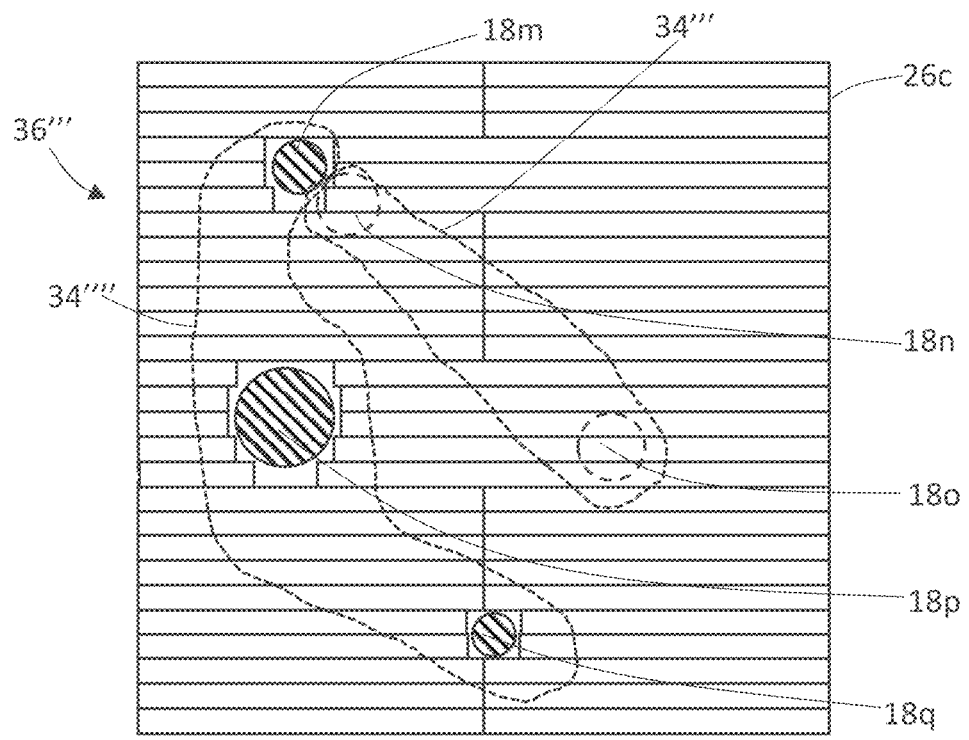

FIG. 5a discloses an MLC opening 26b comprising leaf pairs 40, which leaf pairs 40 are designed to block radiation coming from the radiation source in the MLC 4 (not shown in FIG. 5a). In FIG. 5a five (5) targets 18m-18q are illustrated, here in the form of spherical targets. In FIG. 5a all targets 18m-18q are irradiated as a simulation, not in practice. The analysis of the resulting irradiated areas results in an ENTA 42, which is called a bridge gap opening 42. This area in between target 18p and 18o is not to be irradiated during treatment but in case such an MLC opening 26b as shown in FIG. 5a is to be used, would be irradiated. By grouping the targets 18m-18q into a target partition 36''' comprising two groups 34''', 34'''', whereby a first group 34''' comprises targets 18n and 18o and a second group 34'''' comprises targets 18m, 18p and 18q, as shown in FIG. 5b, it is possible to avoid the bridge gap opening 42 and thereby the ENTA 42 can be avoided. The method according to the enclosure takes such ENTA's 42 into account when finding the best possible target partition 36''' as shown in FIG. 5b. In FIG. 5b the radiation treatment or at least the simulation of the treatment or MLC opening 26c of the second group 34'''' is illustrated, while in FIG. 5c the radiation treatment or at least the simulation of the MLC opening 26d of the first group 34''' containing targets 18n, 18o, is shown.

Figure 5C:
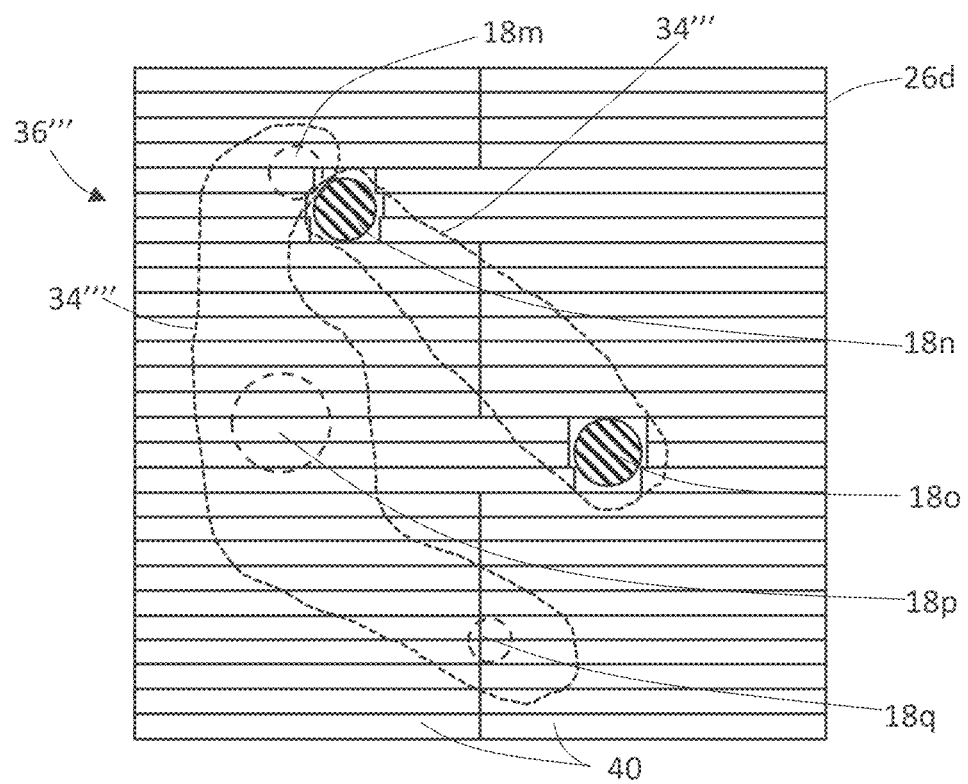

FIGS. 5b and 5c illustrate how the leaf pairs 40 can be closed over the target group 34''', 34'''' that is not to be treated, while there are open over the targets or target group 34''', 34'''' that is to be treated. It is further to be noted that FIGS. 5a to 5c do not illustrate a change in collimator angle 12 to facilitate the illustration, it is however conceivable and falls within the scope of the invention that a target partitioning step may include the checking and consideration of various collimator angles 12 at the control points 28 (c.f. FIG. 2). In FIG. 5b the second target group 34'''' is treated, while in FIG. 5c the first target group 34''' is treated and therewith the expose or the ENTA 42 (c.f. FIG. 5a) is avoided.

Figure 6A:
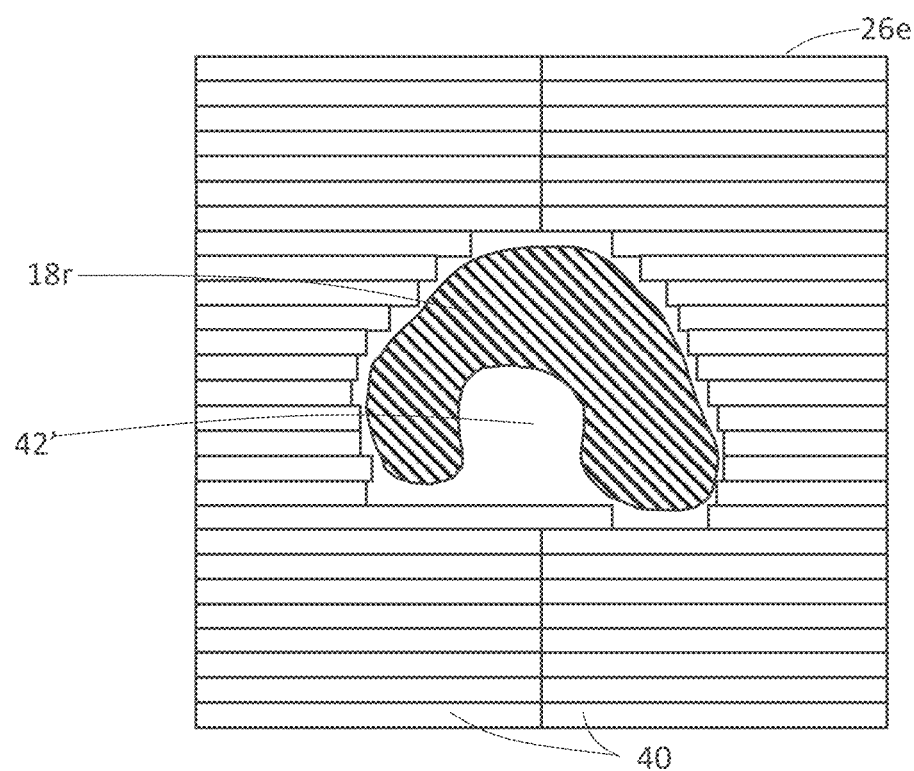

Another example of avoiding ENTA 42 areas is shown in FIGS. 6a and 6b, which figures illustrate another MLC opening 26e, which may illustrate a simulation or a real treatment, in which a target 18r, or a tumor 18r with a banana shape is illustrated. As shown in FIG. 6a, the leaf pairs 40 are opened over the target 18r while the collimator angle (not illustrated) is 0°. For the sake of illustration, we herewith assume that this angle is 0° it may be any other angle depending on how the collimator angle is defined. FIG. 6a illustrates how the ENTA 42' would be exposed (simulation) or is exposed (real treatment) to radiation with the current collimator angle. By rotating the MLC with approximately 90°, as shown in FIG. 6b, the ENTA 42' can be avoided due to the leaf pair configuration and the MLC configuration by using another MLC opening 26f.

In the MLC opening 26f of FIG. 6b, the same target 18r as shown in FIG. 6a is treated, while the MLC is rotated by about 90°. As mentioned, this avoids the exposure of radiation to ENTA's 42'. Also such problems are taken into account when the method according to the disclosure herein is evaluating MLC angles 12 and optimizing the treatment plan.

Exposing ENTA's 42, 42' as illustrated in FIGS. 5a to 6b may be represented in the optimization of the treatment plan by adding an ENTA cost to the optimization for each exposure of ENTA when target partitions 36, 36', 36", 36''' and therewith various target groups 34. 34', 34", 34''' are analysed for finding the optimal target partition 36, 36', 36", 36'''.

An additional cost that may be added to the optimization procedure is illustrated in FIGS. 7a and 7b. FIG. 7a illustrate an MLC opening 26g that is used for a target 18s having a certain shape. The MLC opening 26g illustrated in FIG. 7a is a conformal MLC opening 26g in that the leaf pairs 40 are open over the entire target 18s, while in FIG. 7b the leaf pairs 40 of the MLC opening 26h are not open over the entire target 18s, which means that the MLC opening 26h of FIG. 7b is not conformal and a so-called jagged opening. A jagged MLC opening 26h is avoided in the method according to the disclosure herein. If a jagged MLC opening 26h occurs even though the optimization is run, then such a jagged MLC opening 26h may be weighed into the optimization procedure by adding a cost for a jagged MLC opening at one or some control points 28 (c.f. FIG. 2). The reason why jagged MLC openings 26h should be avoided is because such jagged MLC openings 26h affect the robustness of the dose delivery in a negative manner. It can become uncertain if the dose calculation is correct since it can be unsure whether or not the patient is positioned exactly as assumed when computing the dose.

Figure 8:
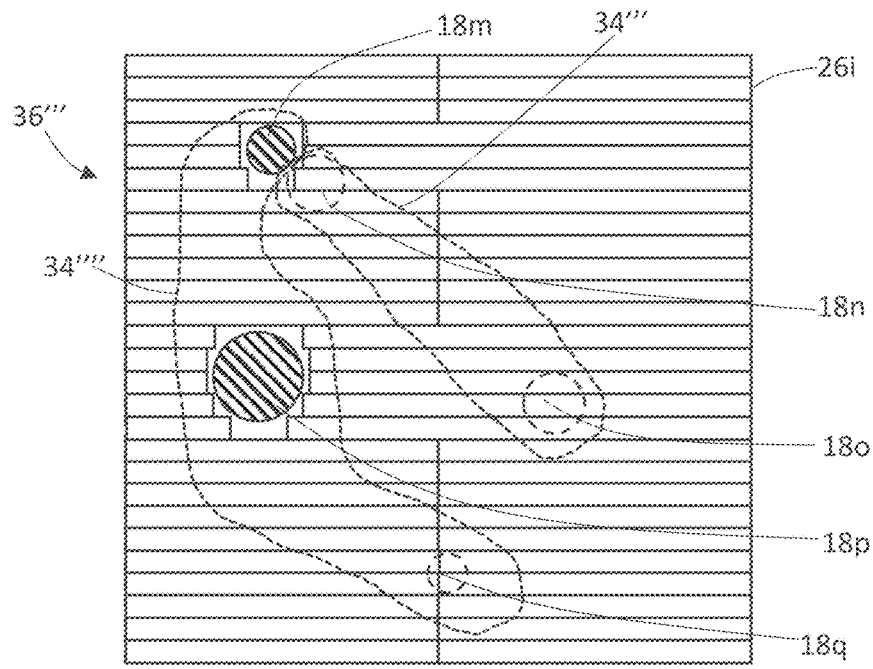
FIG. 8 schematically illustrates another embodiment according to the invention, which embodiment relates to dose control blocking.

A challenge with conformal arc plans is in some cases that does levels for the different targets with the same arc beam become highly correlated and it is thus difficult to obtain desired dose levels of multiple targets, thus targets in one target group simultaneously. Some solutions suggesting VMAT to optimize dose levels but VMAT leads to jagged leaf positions, which needs to be avoided in conformal arc plans or in conformal radiation therapy treatments. FIG. 8 illustrates a similar view as FIG. 5b, however with a different MLC opening 26e. The second target group 34'''' comprising the targets 18m, 18p and 18q is now exposed to radiation but only targets 18m and 18p and not target 18q. Target 18q is blocked from radiation in this particular control point 28 or arc beam 24 (c.f. FIG. 2), since the optimization procedure has shown that target 18q would otherwise receive a dose level that exceeds the desired dose level. This procedure is called dose control blocking and disclosed herein as a third aspect of the invention. The skilled person may understand that is possible to block other targets of the second group 34'' '' in other arc beams 24 along the arc path 20 in order to achieve desired dose levels in the targets of a target group 34, 34', 34''', 34''''.

The optimization procedure according to the third aspect may include segment weight optimization, also called control point MU optimization, to compute and optimize dose levels as far as possible. The differences between the actual dose levels in the targets 18a-18q and the desired dose levels or the dose level goals are computed. The segment weights or arc beam MUs are then increased so that all the actual dose levels of the targets 18a-18q are at or above their dose goals. Then, the target 18q or targets with a dose level that is now higher than the dose level goal are blocked according to the concept illustrated in FIG. 8 over at last a part of the arc path 20 and thus at some of the arc beams 24 or segments. This is done by analyzing the arc beams 24 along the arc path 20 and modifying the arc beams 24 so that the desired dose level is achieved in the respective target 18q by modifying the configuration of the MLC 4 at some of the control points 28 by closing the leaves 40 of the MLC 4 over the relevant target 18q. This procedure allows to lower the actual delivered dose level for each target to the desired dose level.

The procedure relating to dose control blocking according to a third aspect of the invention may be done after the clustering according to FIGS. 4a and 4b is performed and also after the target partitioning according to FIGS. 3a and 3d is done taking into account the avoidance of bridge gap openings 42 or ENTA's 42'. The dose control blocking according to FIG. 8 may however also be done with other treatment planning methods and it is not limited to be only used with the first and second aspect disclosed herein.

Figure 9:
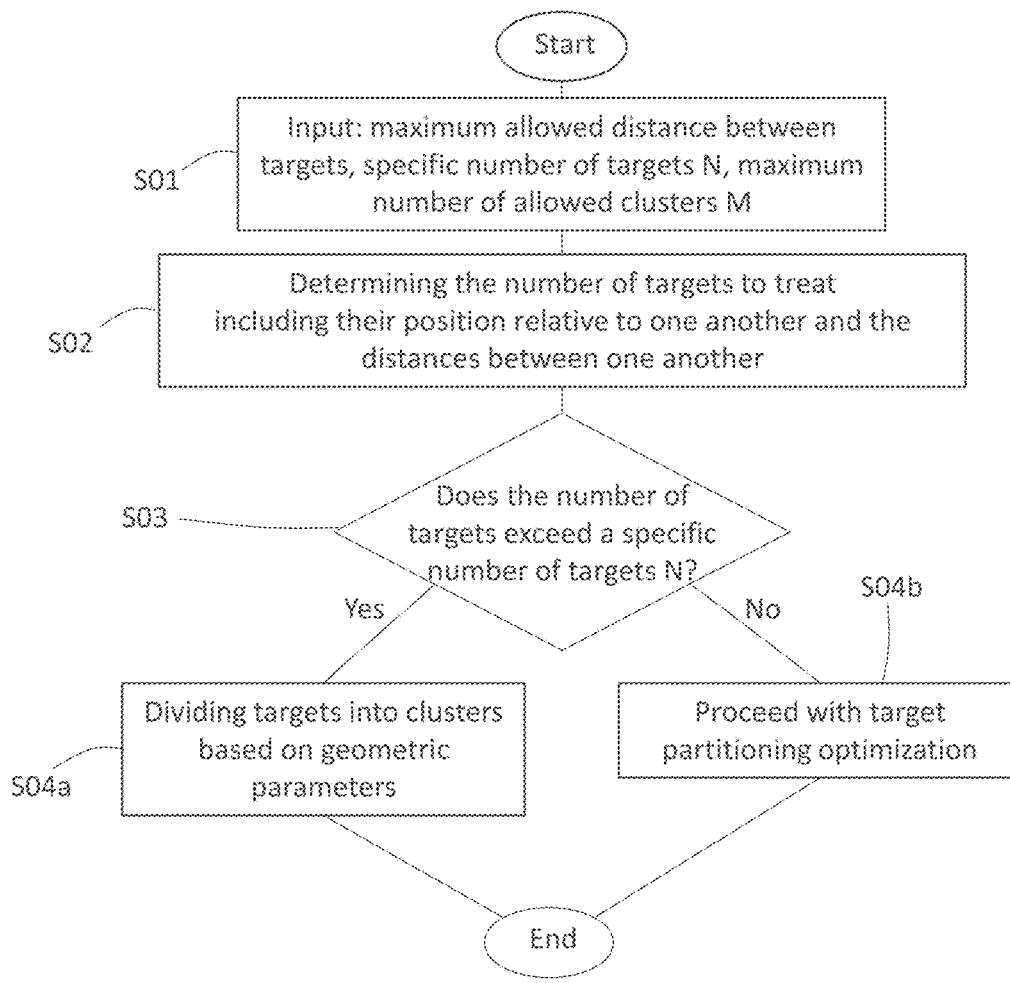
FIG. 9 schematically illustrates an embodiment of a method according to a second aspect of the invention.
Figure 10:
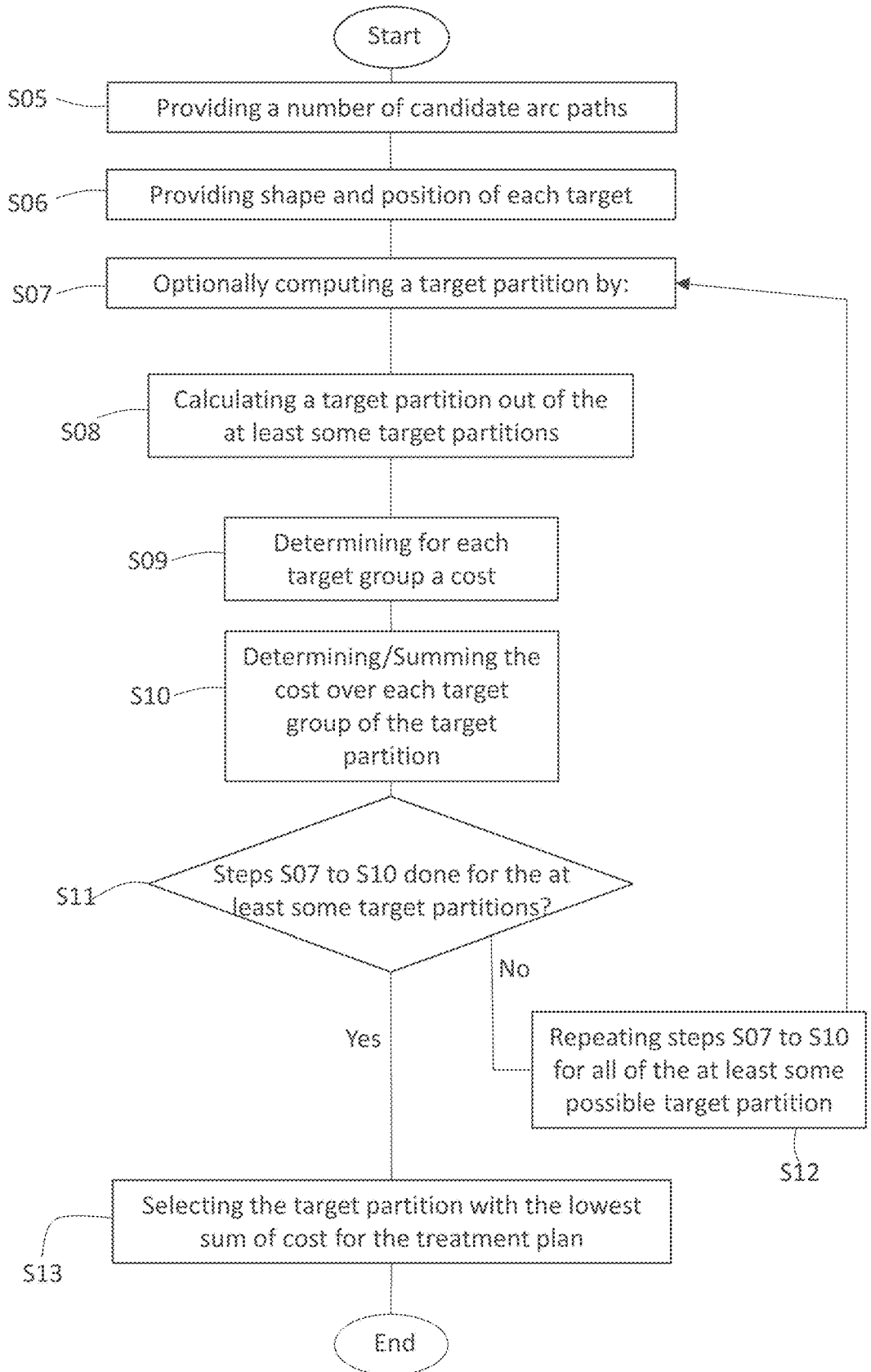
FIG. 10 schematically illustrates another embodiment of a method according to a first aspect of the invention.
Figure 11:
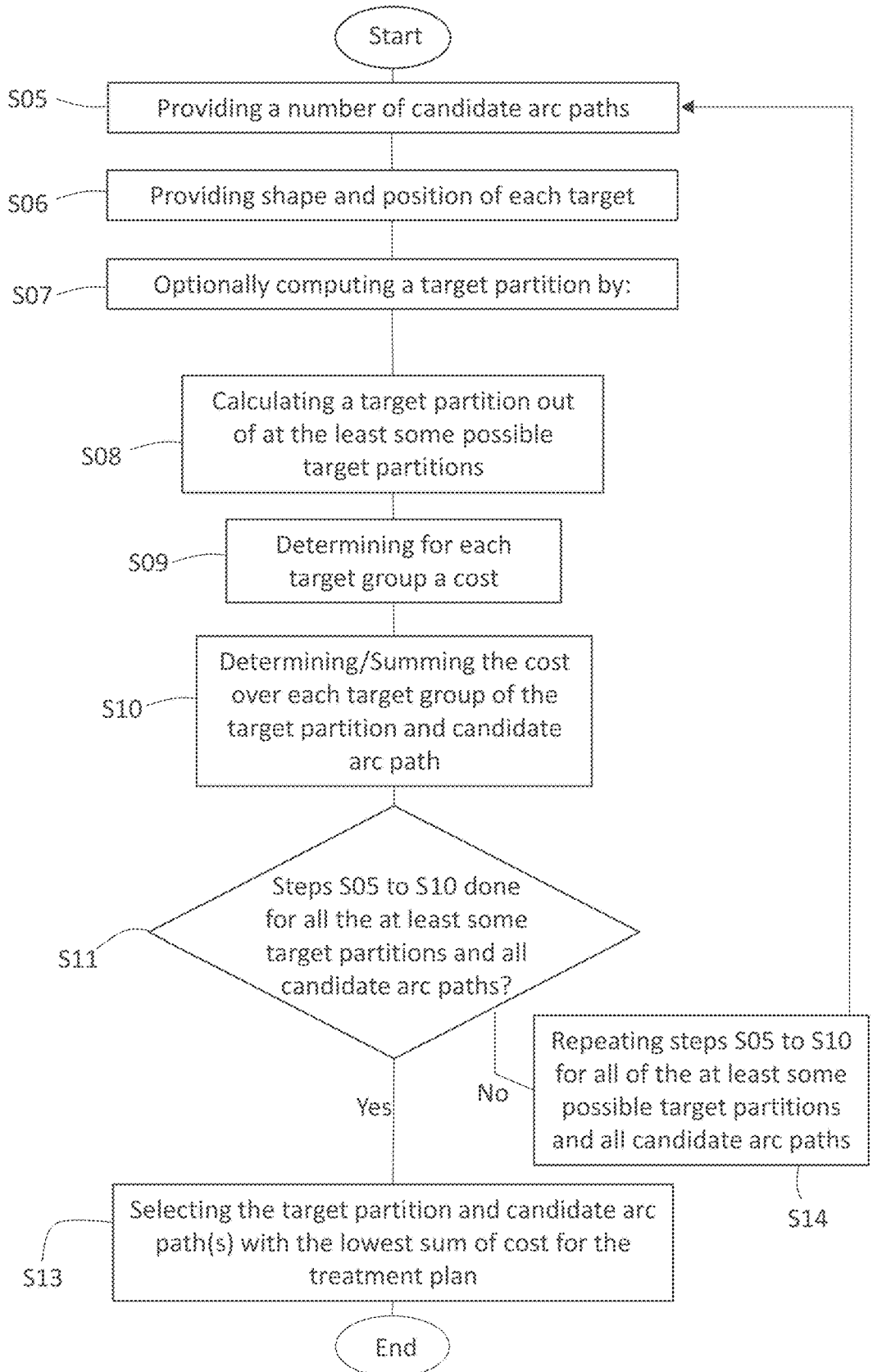
FIG. 11 schematically illustrates another embodiment of a method similar to FIG. 10 using all candidate arc paths.

Since the various aspects and concepts of the present invention have now been described relating to FIGS. 1 to 8, the methods according to aspects of the present invention are herewith explained referring to FIGS. 9 to 11.

FIG. 9 illustrates a method relating to a clustering of targets. A clustering method can be performed prior to the target partitioning. As input S01 into the method a maximum allowed distance between two targets of the same cluster is given. This maximum allowed distance may be a threshold value. Further as another input a specific number of targets N may be given. N may be an integer number such as four (4), five (5) or six (6) targets. Preferably the maximum allowed distance is the main criteria in for selecting clusters. In addition, an input S01 may be given as the maximum number M of clusters 38, 38' for the clustering steps or method. Another potential input is a maximum distance between two targets in one cluster to that the cluster can be determined and chosen based on geometric conditions. Alternatively, a maximum volume may be used as input for the method. Once, the method receives these conditions it determines S02 the number of targets to treat including their position relative to one another and then checks S03 if the number of targets exceed the specific number of targets N. If the specific number N of targets is exceeded the targets are divided S04a into clusters based on geometric parameters such as maximum distance between two targets of the same cluster 38, 38' a volume in which all the targets of one cluster 38, 38' need to fit. In case the number of targets does not exceed the specific number N, the method according to FIG. 10 may be performed.

The method according to FIG. 9 is also explained referring to FIGS. 4a and 4b.

FIG. 10 illustrate a target partitioning optimization method when several targets 18, 18', 18a-18q need to be treated during one radiation treatment. A treatment planning method for generating a treatment plan for radiation therapy where a set of targets 18a-18q are to be treated, the method using a multi-leaf collimator (MLC) 4 for shaping the arc beam 24 or radiation beam 15, a gantry 2 comprising the MLC 4, the gantry 2 capable of rotating at least partially around a patient, a couch 6 for positioning the patient, the MLC 4 defining a collimator angle 12, the gantry 4 being movable around a gantry angle 10 and the couch 6 being movable around a couch angle 8. The target partitioning optimization method comprises the steps of:

Providing S05 a number of candidate arc paths having an isocenter and a maximum number of arc beams for the treatment plan and, depending on the maximum number of arc beams, a maximum number of target groups 34, 34', 34'', 34''', 34'''' allowed for the treatment;

Providing S06 a shape and position of each target 18a-18q of the set of targets;

Optionally computing S07 at least some possible target partitions 36, 36', 36'' for the set of targets, each of the possible target partitions 36, 36', 36'' comprising target groups 34, 34', 34'', 34''', 34'''' whereby each target 18a-18q is part of at least one target group 34, 34', 34'', 34''', 34''''; In addition and as an option, the target partitions that comprise target groups that have been determined not to be optimal, meaning which target groups add a high cost to the target partition at hand, may be directly disregarded from the possible target partitions;

Calculating S08 a target partition 36, 36', 36'' out of the at least some possible target partitions 36, 36', 36'' out of at least some possible target partitions of the set of targets based on a current candidate arc path 20, 20', 20'', 22, the at least some target partitions 36, 36', 36'' comprising a maximum number of target groups 34, 34', 34'', 34''', 34'' '', optionally depending on the constraint of a maximum number of target groups for all arc beams/the number of arc beams;

Determining S09, for each target group 34, 34', 34'', 34''', 34'''' of the possible target partition, a cost, taking into account the current candidate arc path at least one gantry angle 10 and at least one MLC angle 12 for each target group 34, 34', 34'', 34''', 34'''' of a possible target partition 36, 36', 36''';

Determining S10 a cost for the possible target partition 36, 36', 36" and the current candidate arc path by summing the costs of the target groups 34, 34', 34", 34''', 34'''' of the possible target partition 36, 36', 36";

Determining S11 whether or not all of the at least some target partitions 36, 36', 36" have been taken into account;

Repeating S12 the calculating, determining and summing step for each possible target partition and each candidate arc path, and Selecting S13 the optimal target partition 36, 36', 36", arc path 20 and arc beams 24 with the lowest sum of cost for the treatment plan, taking into account the maximum number of target groups over all arc beams.

The method illustrated in FIG. 10 and explained in the foregoing paragraph connects and uses the concepts of arc paths 20, 20', 20" and control points 28 illustrated and explained referring to FIG. 2, the concept of target partitioning illustrated and explained referring to FIGS. 3a to 3d and the concept of avoiding ENTA's 42, 42' by defining a cost for such ENTA's 42, 42' as illustrated and explained referring to FIGS. 5a to 6b. In addition, although not explicitly described in the method according to FIG. 10, the method is designed to be used with conformal treatment and therewith avoids jagged MLC openings as illustrated and explained referring to FIGS. 7a and 7b.

A constraint for the above method may be to provide the total number of target groups over all arc beams. This may help to consider all potential arc beams at once.

Each arc beam 24 along the arc path 20 takes the collimator angle 12 along the arc path 20 and or at each control point 28 into account.

In an embodiment the calculating step S08 may consider all possible target partitions.

From the method according to FIG. 10 an arc plan may be provided based on the optimal target partition 36, 36', 36". Such an arc plan may comprise a series of arc paths 20, 20', 20" used for the treatment of the target groups 34, 34', 34", 34''', 34'''', said arc path comprising information about collimator angles 12, couch angles 8 and MLC openings 26a-26i and other parameters for each arc beam 24 or control point 28. The arc plan provided by the method according to FIG. 10 may comprise the lowest cost arc paths or lowest arc beams based on the optimal target partitions 36, 36', 36". The arc plan may further comprise a computed or desired dose for each target.

FIG. 11 illustrates a similar method scheme as FIG. 10 for a target partitioning optimization method when several targets 18, 18', 18a-18q need to be treated during one radiation treatment. A treatment planning method for generating a treatment plan for radiation therapy where a set of targets 18a-18q are to be treated, the method using a multi-leaf collimator (MLC) 4 for shaping the arc beam 24 or radiation beam 15, a gantry 2 comprising the MLC 4, the gantry 2 capable of rotating at least partially around a patient, a couch 6 for positioning the patient, the MLC 4 defining a collimator angle 12, the gantry 4 being movable around a gantry angle 10 and the couch 6 being movable around a couch angle 8. The target partitioning optimization method comprises the steps of:

Providing S05 a number of candidate arc paths having an isocenter and a maximum number of arc beams for the treatment plan and, depending on the maximum number of arc beams, a maximum number of target groups 34, 34', 34", 34''', 34'''' allowed for the treatment;

Providing S06 a shape and position of each target 18a-18q of the set of targets;

Optionally computing S07 at least some possible target partitions 36, 36', 36" for the set of targets, each of the possible target partitions 36, 36', 36" comprising target groups 34, 34', 34", 34''', 34'''' whereby each target 18a-18q is part of at least one target group 34, 34', 34", 34''', 34''''; In addition and as an option, the target partitions that comprise target groups that have been determined not to be optimal, meaning which target groups add a high cost to the target partition at hand, may be directly disregarded from the possible target partitions;

Calculating S08 a target partition 36, 36', 36" out of the at least some possible target partitions 36, 36', 36" out of the set of targets, based on a current candidate arc path 20, 20', 20", 22, the at least some possible target partitions 36, 36', 36" comprising a maximum number of target groups 34, 34', 34", 34', 34'''', taking into account the candidate arc path at least one gantry angle 10 and at least one MLC angle 12 for each target group 34, 34', 34", 34', 34'''' of a possible target partition 36, 36', 36";

Determining S09, a cost for each target group 34, 34', 34", 34''', 34'''' of the possible target partition 36, 36', 36", taking into account the current candidate arc path 20, 20', 20", 22, at least one gantry angle 10 and at least one MLC angle 12 for each target group 34, 34', 34", 34''', 34'''' of a possible target partition 36, 36', 36";

Determining S10 a cost for the possible target partition 36, 36', 36" and current candidate arc path by summing the costs of the target groups 34, 34', 34", 34''', 34'''' of the possible target partition 36, 36', 36";

Determining S11 whether or not all of the at least some possible target partitions 36, 36', 36" and candidate arc path have been taken into account;

Repeating S14 the providing candidate arc paths, providing shape and position, optionally computing, calculating, determining and summing step for each possible target partition and each or at least some candidate arc path, and Selecting S13 the optimal target partition 36, 36', 36", arc path 20 and arc beams 24 with the lowest sum of cost for the treatment plan and optionally taking account restrictions or constraints relating to a maximum number of total target groups when summing over the at least some target partitions.

The above method and as illustrated in FIG. 11 allows to take each candidate arc path and all of the at least some target partitions into account for the optimizing step, at least more or less simultaneously thereby aiming for the best possible treatment plan.

Figure 12:
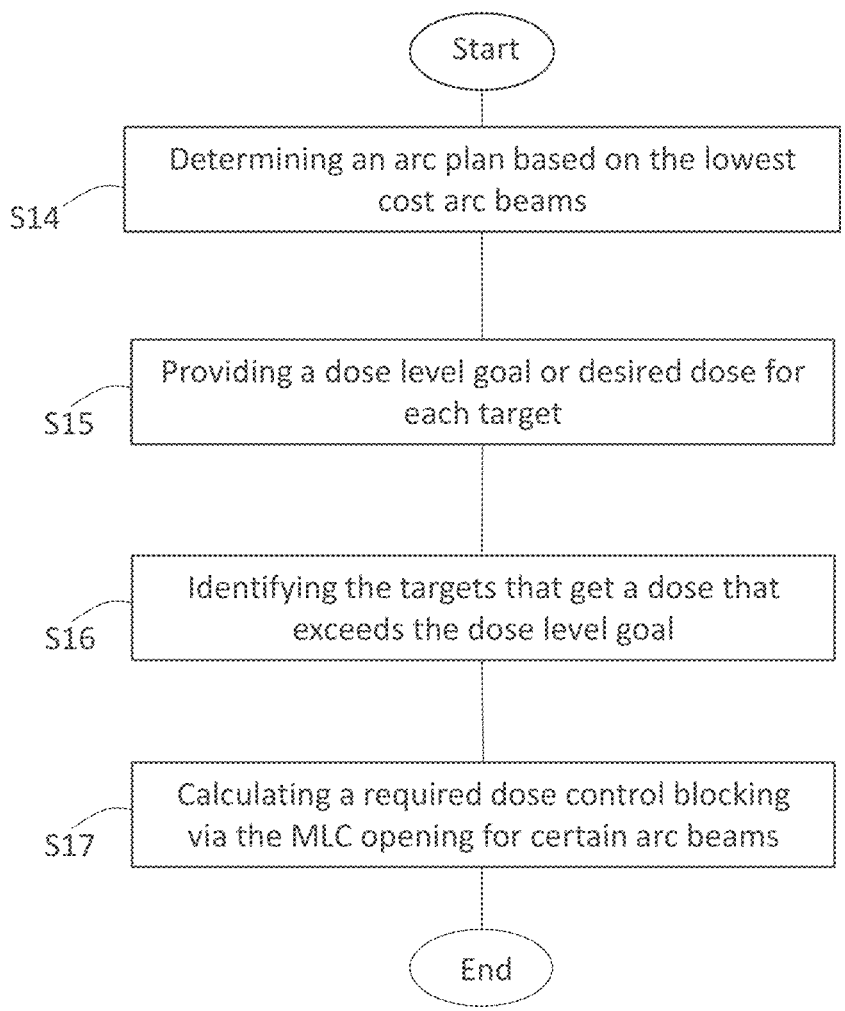
FIG. 12 schematically illustrates still another embodiment of a method according to a third aspect of the invention.

FIG. 12 further illustrates a method according to the third aspect of the invention relating to the method of dose control blocking. The does control blocking method comprises the steps of:

Determining S14 an arc plan based on the lowest cost arc beams 24 or lowest cost arc paths 20, 20' 20", the arc plan comprising a computed dose for the treatment;

Providing S15 a dose level goal for each target of the target groups 34, 34', 34", 34''', 34'''' of the optimal target partition 36, 36', 36" and determining exposure times and monitoring units for each target so that each target of the optimal target partition 36, 36', 36" gets at least the desired dose level;

Identifying S16 the targets that get a dose level that exceeds the dose level goal; and Calculating S17 a required dose control blocking where leaves of the MLC opening are entirely closed for targets with a dose level that exceeds the dose level goal at certain arc beams 24 or parts of the arc beams 24, in order to control the delivery of the dose and therewith the dose level in these targets.

The method according to FIG. 11 may be used with the invention disclosed here or it may be used with another treatment planning method. Advantageously the dose control blocking method is used in conformal arc beam treatment or arc plans.

Figure 13:
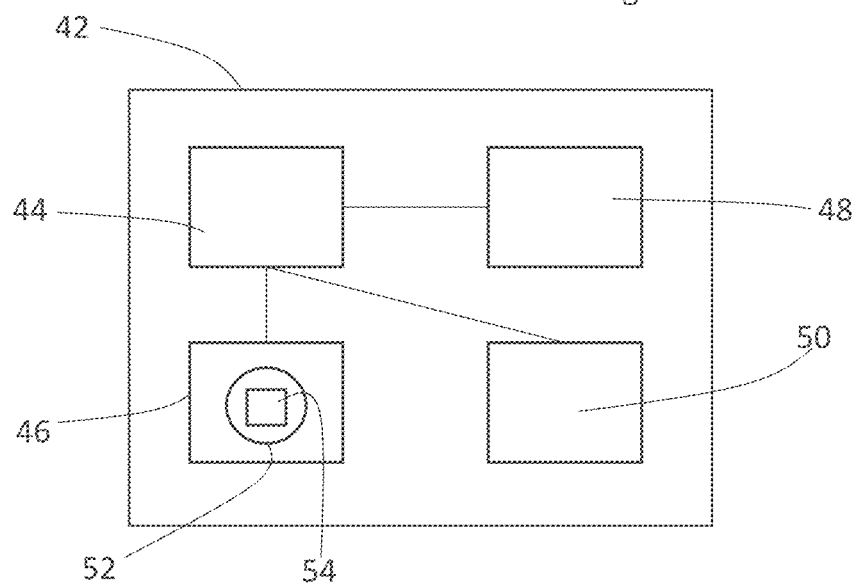
FIG. 13 schematically illustrates a radiation treatment planning system.

FIG. 13 illustrates further a radiation therapy treatment planning system 42 comprising a processor 44, a memory 46 connected to the processor 44, an optional extra memory 50 also connected to the processor 44 and/or the memory 46 and an input/output interface 48 having a display and/or a keyboard for user interaction. The processor 44 may be any combination of a central processing unit (CPU), multiprocessor, digital signal processor (DSP), an ASIC (application specific integrated circuit) capable of executing software instructions stored on the memory and capable of executing the methods described according to the embodiments herein. The memory 46 and/or the extra memory 50 may comprise software code in the form of a computer program product 52 comprising computer software 54 or instructions that comprise any method according to this disclosure. The computer software 54 may be executed by the processor 44.

The memory 46 and the extra memory 50 may be any of a random-access memory (RAM) or read only memory (ROM) or any combination thereof.

EXAMPLES

Example 1

Suppose that four (4) candidate arc paths are provided to treat a set of targets. We assume for this example that each target is to be treated from all four (4) couch angles, which correspond to the provided candidate arc paths. Further it is assumed in this example 1 that each target is treated exactly once from each such couch angle/candidate arc path.

The objective is to find the best possible plan using at most ten (10) arcs in the final plan, which means the total number of target groups is at most 10 over all candidate arc paths. If we can lower the number of arcs, for instance to nine (9) or eight (8), while still having the optimal partition's ENTA to be at a satisfactory level, for example at or below some low threshold value, such as 0.5 cm², such an optimization must be considered as well. In other words, we are allowed, subject to for example a clinic's guidelines, to use ten (10) arcs, but would prefer to use fewer if that would not significantly increase the dose of radiation to non-target tissue.

The optimization of this problem must be done simultaneously for all candidate arc paths. The reason for this is that if we try to do it one arc at a time, then we can find the optimal partition into, for instance, two (2), three (3), or four (4) target groups for the first candidate arc path. The ENTA decreases (if not already satisfactory) when we increase the number of target groups, so we could be tempted to divide the set of targets into four (4) target groups for the first candidate arc path. On the other hand, that leaves only six (6) target groups left for the 3 remaining candidate arc paths. Dividing into just two (2) target groups leaves eight (8) to spare but induces a higher ENTA contribution. However, at this point in time the best configuration of candidate arc path and target partitioning is not known, which means it is impossible to know what the optimal choice is.

On the other hand, if we optimize simultaneously, we start by computing the optimal partitions into, e.g., two (2), three (3), and four (4) target groups for each of the four (4) candidate arc paths, saving the cost of the optimal partitions for each candidate arc path and number of target groups. From this, we loop over all ways of combining four numbers (one for each candidate arc path) all either two (2), three (3), or four (4), so that their sum is ten (10). Some examples are: 2+2+2+4; 2+3+2+3; 3+3+2+2. These options are then evaluated by summing the ENTA contribution for each candidate arc path; in the case 2+2+2+4, we sum the ENTA of the optimal way of partitioning each of the first three candidate arc paths into two (2) target groups each, with the ENTA of the optimal way of partitioning the fourth part into four (4) target groups. Doing this for all the possible combinations and choosing the lowest sum gives us the optimal way of partitioning the targets optimally for all candidate arc paths. We then compare the total ENTA for this optimum with a threshold value. If low enough, thus if the ENTA is at or below the threshold, we can hope it still is low enough even for nine (9) beams in total; to find out, we repeat the same process as above, but with the sum of the number of target groups restricted to being nine (9) instead of ten (10). If the total ENTA is low enough for nine (9) we can do it again for eight (8), and so on. This way we end up with the optimal treatment plan using at most ten (10) candidate arc paths, reducing the number of final arc paths if possible, without significantly affecting the ENTA.

Example 2

Suppose again that we have four (4) candidate arc paths, but this time we don't require each target to be treated by each candidate arc path, but rather by at least three (3) of them. However, the set of arc paths treating a target A does not have to be the same as the set of arc paths treating another target B. Note that this example works just as well, and is useful in practice, also in other situations, for instance if we have a maximum of five (5) candidate arc paths and want to treat each target from at least four (4) or at least three (3) of the candidate arc paths.

Suppose we want to treat six (6) targets with as few arc beams as possible, while keeping the total ENTA below a threshold value. The fact that we allow to treat from only three (3) out of the four (4) available candidate arc paths per target, enables the possibility to use fewer beams, while getting a better or, in the worst case, an equally good, plan compared to manually selecting three (3) of the four (4) candidate arc paths and using only those candidate arc paths for treating all targets.

To do this we proceed in a similar way to the previous example, computing costs for the optimal ways of partitioning into two (2), three (3), and four (4) parts (we could also partition into one (1) or five (5) parts) for each of the candidate arc paths. However, this time we add another level of optimization: that of choosing which of the at least three (3) out of the four (4) candidate arc paths that are to treat each target.

In the previous example 1, the computation of costs for the optimal ways of partitioning into two (2), three (3), and four (4) target groups all assume all our targets are included in one of the target groups of the partition. Now we do these computations not only for the set of all targets, but also for each subset of targets. In other words, for each subset of targets we find the optimal ways of partitioning that subset into two (2), three (3) and four (4) target groups, given the restriction that enough targets are in the subset.

Suppose we have 6 targets: A, B, C, D, E, F. For each candidate arc path, we do the following:

Enumerate all subsets of the set S={A, B, C, D, E, F} of all targets. One such subset is S1={A, B, D, F}, where C and E is missing; another subset is S2={B, C}; yet another subset is the set S3={A, B, C, D, E, F} which is equal to S itself.

For each subset, find the best partitions into two (2), three (3) and four (4) target groups. For S1 this might result in:
two (2) target groups: {{A, D}, {B, F}}, total cost 2.1
three (3) target groups: {{A, D}, {B}, {F}}, total cost 0.3
four (4) target groups: {{A}, {D}, {B}, {F}}, total cost 0.0

For S2, which contains only two (2) targets, it does not make sense to divide into three (3) or four (4) target groups, so we just find the best way of dividing it into two target groups.

Having done the previous for each candidate arc path is it time to combine the results into the optimal treatment plan. We do this by solving the problem for a multitude of choices for the total number of arc paths, similar to the previous example 1, where those choices were ten (10) arc paths, nine (9) arc paths, and eight (8) arc paths. We then minimize the number of arc paths under the constraint that the total cost must be below a threshold value.

However, in this setting that problem is more complex. Suppose for the case of this example 1 that we are looking at just the case where the total number of arcs in the final plan should be ten (10). Then, for each of the possible ways of choosing partition sizes per candidate arc path that sum to ten (10), for instance 2+2+2+4, we need to consider all ways of choosing different subsets to consider for each partition. That is, we need to compute one cost for each combination of ways we can choose subsets for the different candidate arc paths. For instance, we need to compute one sum of cost if the subsets chosen are S3, S3, S3, S3; one for S2, S3, S3, S3; one for S1, S3, S3, S3; and so. Doing this we only consider the combinations that fulfil the requirement of at least three (3) initial arc paths per target: as such, S1, S2, S3, S3 is not considered, since target E is not included in S1 or S2, and hence only treated by two candidate arc paths, namely the third and fourth one, which both treat S3.

Having done this for all valid choices of combinations of subsets, one assigns, as the cost for the division into 2+2+2+4 target groups, the lowest cost among the valid subset choices. After doing this for all possible partition sizes per candidate arc path adding up to ten (10) arc paths we have found the best way of treating using ten (10) arc paths with at least three (3) candidate arc paths treating each target. Repeating this for different numbers of total number of arc paths, just as in the previous example 1 gives the result we are looking for.

For example, the result in this case could be that we end up with the treatment of subsets S3, S1, S3, S4, where S4={B, C, E}, with divisions into 3, 2, 2, 2 target groups respectively, giving 9 arc paths in total, and a cost of 0. Doing this while requiring every candidate arc path to treat each target, as in example 1, would be equivalent to treating with subsets S3, S3, S3, S3. Replacing S1 and S4 with instances of S3 would increase the cost of treating these target partitions when dividing them into 2 target groups each. Therefore, and in order to achieve a cost of 0 in this case the number of target groups in these partitions increase and thus the total number of arc paths in the plan increase as well to 10 or 11 in order to achieve a cost of 0.

The invention has now been described referring to embodiments disclosed above and in the enclosed figures. However, and as the skilled person may understand other embodiments than the ones disclosed herein may be conceivable and are equally possible within the scope of the invention, as defined by the appended patent claims.

The invention claimed is:

1. A treatment planning method for generating a treatment plan for radiation therapy where a set of targets are to be treated, the method using a multi-leaf collimator (MLC) for shaping an arc beam, a gantry for holding the MLC, the gantry capable of rotating at least partially around a patient, a couch for positioning the patient, the MLC being movable and defining a collimator angle, the gantry being movable and defining a gantry angle and the couch optionally being movable thereby defining a couch angle, the method comprising the steps of:

providing a number of candidate arc paths having an isocenter and a maximum number of arc beams for the treatment plan and, depending on the maximum number of arc beams, a maximum number of target groups;

providing a shape and position of each target of the set of targets;

calculating a target partition out of at least some possible target partitions of the set of targets based on a current candidate arc path, the at least some possible target partitions comprising a maximum number of target groups, each of the at least some possible target partitions comprising target groups;

determining a cost for each target group of the possible target partition, taking into account the current candidate arc path, at least one gantry angle and at least one MLC angle for each target group of a possible target partition;

determining a cost for the possible target partition and current candidate arc path by summing the costs of the target groups of the possible target partition;

repeating the calculating, determining and summing step for each of the at least some possible target partitions and at least some of the candidate arc paths, and selecting the optimal target partition and candidate arc paths with the lowest sum of cost for the treatment plan.

2. The treatment planning method of claim 1, wherein the calculating step further takes at least one couch angle into account.

3. The treatment planning method of claim 1, wherein the maximum number of target groups is provided by the treatment planner or any given number from 2 to 30, preferably 8 to 20 for all arc beams alternatively 1 to 6 target groups per arc beam.

4. The treatment planning method of claim 1, wherein the calculating step further includes dividing the candidate arc path into control points spaced at regular intervals, each interval corresponding to a gantry angle segment, wherein at each control point an optimal MLC angle and/or an optimal couch angle is calculated.

5. The treatment planning method of claim 1, wherein for each control point an optimal MLC opening is calculated, whereby the optimal MLC opening is chosen based on lowest cost and optimal MLC angle versus previous and following MLC angle(s) at the previous and following control point.

6. The treatment planning method of claim 1, wherein the calculating step further includes dividing the candidate arc path into control points spaced at regular intervals, each interval corresponding to a gantry angle segment, wherein the MLC angle is kept in a fixed position for each control point and wherein the cost for each candidate MLC angle is calculated for each control point to find an optimal fixed MLC angle for each candidate arc path.

7. The treatment planning method of claim 4, wherein an additional cost is added if the MLC angle needs to be changed in between neighboring control points.

8. The treatment planning method of claim 2, wherein an additional cost is added if the couch angle needs to be changed in between neighboring control points.

9. The treatment planning method of claim 1, wherein an additional cost is added, if the total number of target groups in a current target partition exceeds a certain threshold value, such as 15 to 20 target groups.

10. The treatment planning method of claim 1, wherein the maximum number of arc beams corresponds to the maximum number of target groups.

11. The treatment planning method of claim 1, wherein the arc beams are conformal arc beams.

12. The treatment planning method of claim 1, further comprising the step of retrieving the lowest cost arc beam with the lowest cost MLC angle and gantry angle pairs for each target group of the optimal target partition and delivering these lowest cost arc beams, whereby each arc beam is conformed to one target group of the optimal target partition so that each target group receives one arc beam for treatment.

13. The treatment planning method of claim 1, further comprising the step of using the treatment planning method according to claim 1 as a starting point for volumetric modulated arc therapy optimization.

14. The treatment planning method of claim 1, wherein the at least some possible target partitions are considered for various candidate arc paths and providing an arc plan comprising arc beams and arc paths, based on the optimal target partitions and lowest cost arc beams, taking into account restrictions over the maximum number of arc beams, such as a maximum number of target groups in total over the maximum number of arc beams.

15. The treatment planning method of claim 1, further comprising the steps of:
receiving an arc plan and a computed dose for each target in the optimal target partition;
providing a dose level goal for each target and adjusting the arc plan so that each target gets at least the dose level goal;
identifying the targets that get a dose level that exceeds the dose level goal; and
calculating a required dose control blocking where at least some leaves of the MLC are entirely closed for at least a part of some arc beams for the targets with a dose level that exceeds the dose level goal in order to optimize the delivery of the dose and therewith the dose level goals for all targets of the optimal target partition.

16. The treatment planning method of claim 11, wherein control points and/or start gantry angle and stop gantry angle are modified so that any fully closed MLC openings at control points or segments, in which all targets are blocked, are avoided.

17. The treatment planning method of claim 1, wherein a clustering step is performed prior to the steps disclosed in claim 1, if the distance between two targets exceeds a certain threshold value or if the number of targets exceeds N targets, whereby N is an integer number, said clustering step comprising the steps of choosing a maximum number M, whereby M is an integer number, of clusters based on the number of targets, restricting the number of targets in a cluster to less or equal than N and choosing the targets in a cluster based on a maximum allowed distance between two targets of the same cluster.

18. The treatment planning method of claim 17, wherein as input a position and a three-dimensional shape of each target of the set of targets relative to the other targets of the set of targets is provided and wherein an operator specifies the integer numbers N and M.

19. A computer program product comprising computer readable means which, when executed in a computer, will cause the computer to perform the method of claim 1.

20. A radiation therapy planning system comprising a processor, a memory, wherein the memory comprises a computer program product of claim 19, the radiation therapy planning system being designed to perform the method of claim 1.

* * * * *